(12) United States Patent
Agah et al.

(10) Patent No.: US 10,695,543 B2
(45) Date of Patent: Jun. 30, 2020

(54) METHODS FOR TREATING CANCEROUS TUMORS

(71) Applicant: RenovoRx, Inc., Los Altos, CA (US)

(72) Inventors: Ramtin Agah, Menlo Park, CA (US);
Kamran Najmabadi, Palo Alto, CA (US); Shaun R. Bagai, Mountain View, CA (US)

(73) Assignee: RenovoRx, Inc., Los Altos, CA (US)

( * ) Notice: Subject to any disclaimer, the term of this patent is extended or adjusted under 35 U.S.C. 154(b) by 293 days.

(21) Appl. No.: 15/807,011

(22) Filed: Nov. 8, 2017

(65) Prior Publication Data

US 2018/0333563 A1  Nov. 22, 2018

Related U.S. Application Data

(60) Provisional application No. 62/507,962, filed on May 18, 2017.

(51) Int. Cl.
*A61M 25/10* (2013.01)
*A61M 25/00* (2006.01)
(Continued)

(52) U.S. Cl.
CPC ... *A61M 25/1011* (2013.01); *A61B 17/12136* (2013.01); *A61K 31/337* (2013.01);
(Continued)

(58) Field of Classification Search
CPC ....... A61M 25/1011; A61M 2025/1013–1015; A61M 2025/1052; A61N 5/10–1084;
(Continued)

(56) References Cited

U.S. PATENT DOCUMENTS

| 4,445,892 A | 5/1984 | Hussein et al. |
| 4,655,746 A | 4/1987 | Daniels et al. |

(Continued)

FOREIGN PATENT DOCUMENTS

| EP | 0402467 A1 | 12/1990 |
| EP | 1303228 B1 | 9/2012 |

(Continued)

OTHER PUBLICATIONS

US 7,316,661 B2, 01/2008, Zadno-Azizi (withdrawn)

(Continued)

*Primary Examiner* — Catherine B Kuhlman
(74) *Attorney, Agent, or Firm* — Shay Glenn LLP

(57) ABSTRACT

Apparatuses and methods described herein relate to treating cancerous tumors using radiation therapy and chemotherapy. In some embodiments, a method of treatment includes administering radiation therapy targeting a tumor, isolating a segment of a vessel proximate to the tumor, and administering a dose of a chemotherapeutic agent to the segment of the vessel. The method can further include waiting a period of time after administering the radiation therapy before administering the dose of the chemotherapeutic agent. In some embodiments, a catheter device including first and second occluding elements can be used to isolate the segment of the vessel.

19 Claims, 13 Drawing Sheets
(3 of 13 Drawing Sheet(s) Filed in Color)

(51) Int. Cl.

| | | |
|---|---|---|
| *A61K 31/7068* | (2006.01) | |
| *A61N 5/10* | (2006.01) | |
| *A61K 31/513* | (2006.01) | |
| *A61K 31/4745* | (2006.01) | |
| *A61K 31/555* | (2006.01) | |
| *A61K 31/436* | (2006.01) | |
| *A61K 31/404* | (2006.01) | |
| *A61P 35/00* | (2006.01) | |
| *A61K 31/337* | (2006.01) | |
| *A61K 31/519* | (2006.01) | |
| *A61K 33/24* | (2019.01) | |
| *A61K 31/407* | (2006.01) | |
| *A61K 31/517* | (2006.01) | |
| *A61K 31/704* | (2006.01) | |
| *A61B 17/12* | (2006.01) | |
| *A61M 31/00* | (2006.01) | |

(52) U.S. Cl.
CPC .......... *A61K 31/404* (2013.01); *A61K 31/407* (2013.01); *A61K 31/436* (2013.01); *A61K 31/4745* (2013.01); *A61K 31/513* (2013.01); *A61K 31/517* (2013.01); *A61K 31/519* (2013.01); *A61K 31/555* (2013.01); *A61K 31/704* (2013.01); *A61K 31/7068* (2013.01); *A61K 33/24* (2013.01); *A61M 25/007* (2013.01); *A61N 5/1002* (2013.01); *A61P 35/00* (2018.01); *A61B 17/12045* (2013.01); *A61B 17/12109* (2013.01); *A61M 31/005* (2013.01); *A61M 2025/1015* (2013.01); *A61M 2025/1052* (2013.01); *A61N 5/10* (2013.01)

(58) Field of Classification Search
CPC ............... A61B 17/12022–12195; A61B 2017/1205–12127
USPC .................................................. 604/101.05
See application file for complete search history.

(56) References Cited

U.S. PATENT DOCUMENTS

| | | |
|---|---|---|
| 4,696,304 A | 9/1987 | Chin |
| 4,714,460 A | 12/1987 | Calderon |
| 4,830,003 A | 5/1989 | Wolff et al. |
| 4,883,459 A | 11/1989 | Calderon |
| 5,281,200 A | 1/1994 | Corso, Jr. et al. |
| 5,318,535 A | 6/1994 | Miraki |
| 5,338,301 A | 8/1994 | Diaz |
| 5,397,307 A | 3/1995 | Goodin |
| 5,411,479 A | 5/1995 | Bodden |
| 5,415,636 A | 5/1995 | Forman |
| 5,419,763 A | 5/1995 | Hildebrand |
| 5,462,529 A | 10/1995 | Simpson et al. |
| 5,478,309 A | 12/1995 | Sweezer et al. |
| 5,484,412 A | 1/1996 | Pierpont |
| 5,514,092 A | 5/1996 | Forman et al. |
| 5,575,815 A | 11/1996 | Slepian et al. |
| 5,772,632 A | 6/1998 | Forman |
| 5,810,757 A | 9/1998 | Sweezer, Jr. et al. |
| 5,833,644 A | 11/1998 | Zadno-Azizi et al. |
| 5,833,650 A | 11/1998 | Imran |
| 5,833,672 A | 11/1998 | Kawata et al. |
| 5,836,905 A | 11/1998 | Lemelson et al. |
| 5,836,967 A | 11/1998 | Schneider |
| 5,840,066 A | 11/1998 | Matsuda et al. |
| 5,843,050 A | 12/1998 | Jones et al. |
| 5,888,530 A * | 3/1999 | Netti ................ A61M 5/14 424/423 |
| 5,916,193 A | 6/1999 | Stevens et al. |
| 5,919,135 A * | 7/1999 | Lemelson ........... A61B 5/055 378/4 |
| 5,919,163 A | 7/1999 | Glickman |
| 5,925,016 A | 7/1999 | Chornenky et al. |
| 5,961,536 A | 10/1999 | Mickley et al. |
| 5,968,012 A | 10/1999 | Ren et al. |
| 6,030,362 A | 2/2000 | Boussignac et al. |
| 6,051,014 A | 4/2000 | Jang |
| 6,083,198 A | 7/2000 | Afzal |
| 6,126,635 A | 10/2000 | Simpson et al. |
| 6,156,053 A | 12/2000 | Gandhi et al. |
| 6,165,152 A | 12/2000 | Becker et al. |
| 6,176,844 B1 | 1/2001 | Lee |
| 6,287,290 B1 | 9/2001 | Perkins et al. |
| 6,299,598 B1 | 10/2001 | Bander |
| 6,346,098 B1 | 2/2002 | Yock et al. |
| 6,351,663 B1 | 2/2002 | Flower et al. |
| 6,375,634 B1 * | 4/2002 | Carroll ............... A61B 18/00 604/19 |
| 6,436,090 B1 | 8/2002 | Sanchez et al. |
| 6,440,097 B1 | 8/2002 | Kupiecki |
| 6,461,327 B1 | 10/2002 | Addis et al. |
| 6,482,172 B1 | 11/2002 | Thramann |
| 6,485,500 B1 | 11/2002 | Kokish et al. |
| 6,488,672 B1 | 12/2002 | Dance et al. |
| 6,508,777 B1 | 1/2003 | Macoviak et al. |
| 6,520,183 B2 | 2/2003 | Amar |
| 6,569,146 B1 | 5/2003 | Werner et al. |
| 6,569,148 B2 | 5/2003 | Bagaoisan et al. |
| 6,575,932 B1 | 6/2003 | O'Brien et al. |
| 6,589,264 B1 | 7/2003 | Barbut et al. |
| 6,592,546 B1 | 7/2003 | Barbut et al. |
| 6,682,499 B2 | 1/2004 | Lenker |
| 6,685,672 B1 | 2/2004 | Forman |
| 6,692,458 B2 | 2/2004 | Forman et al. |
| 6,699,231 B1 | 3/2004 | Sterman et al. |
| 6,702,781 B1 | 3/2004 | Reifart et al. |
| 6,706,013 B1 | 3/2004 | Bhat et al. |
| 6,706,062 B2 | 3/2004 | Vardi et al. |
| 6,712,806 B2 | 3/2004 | St. Germain et al. |
| 6,723,070 B1 | 4/2004 | Arai et al. |
| 6,743,196 B2 | 6/2004 | Barbut et al. |
| 6,749,581 B2 | 6/2004 | Thompson et al. |
| 6,884,233 B2 | 4/2005 | Dance et al. |
| 6,929,633 B2 | 8/2005 | Evans et al. |
| 6,939,320 B2 | 9/2005 | Lennox |
| 6,986,788 B2 | 1/2006 | Paul et al. |
| 6,997,898 B2 | 2/2006 | Forman |
| 7,150,736 B2 | 12/2006 | Barbut et al. |
| 7,179,251 B2 | 2/2007 | Palasis |
| 7,297,475 B2 | 11/2007 | Koiwai et al. |
| 7,452,532 B2 | 11/2008 | Alt |
| 7,503,904 B2 | 3/2009 | Choi |
| 7,537,562 B2 | 5/2009 | Takano |
| 7,645,259 B2 | 1/2010 | Goldman |
| 7,704,220 B2 | 4/2010 | Solar et al. |
| 7,708,715 B2 | 5/2010 | Gellman |
| 7,780,628 B1 | 8/2010 | Keren et al. |
| 7,815,624 B2 | 10/2010 | Larson |
| 7,887,661 B2 | 2/2011 | Chiu et al. |
| 8,043,257 B2 | 10/2011 | Nguyen et al. |
| 8,088,103 B2 | 1/2012 | Teeslink et al. |
| 8,162,879 B2 | 4/2012 | Hattangadi et al. |
| 8,172,792 B2 | 5/2012 | Wang et al. |
| 8,177,829 B2 | 5/2012 | Benson et al. |
| 8,182,446 B2 | 5/2012 | Schaeffer et al. |
| 8,182,463 B2 | 5/2012 | Chiu et al. |
| 8,187,229 B2 | 5/2012 | Weitzner et al. |
| 8,251,948 B2 | 8/2012 | Goldman |
| 8,262,611 B2 | 9/2012 | Teeslink et al. |
| 8,262,613 B2 | 9/2012 | Lennox |
| 8,414,473 B2 | 4/2013 | Jenkins et al. |
| 8,702,678 B2 | 4/2014 | Comerota et al. |
| 8,784,602 B2 | 7/2014 | Schaeffer et al. |
| 8,821,476 B2 | 9/2014 | Agah et al. |
| 8,870,849 B2 | 10/2014 | Steinmetz et al. |
| 9,180,281 B2 | 11/2015 | Gerrans et al. |
| 9,254,210 B2 | 2/2016 | Bourang |
| 9,457,171 B2 | 10/2016 | Agah et al. |
| 9,463,304 B2 | 10/2016 | Agah et al. |
| 10,099,040 B2 | 10/2018 | Agah et al. |
| 2001/0041862 A1 | 11/2001 | Glickman |

(56) References Cited

U.S. PATENT DOCUMENTS

| | | | |
|---|---|---|---|
| 2002/0082548 | A1 | 6/2002 | Sanchez et al. |
| 2002/0107471 | A1 | 8/2002 | Thompson et al. |
| 2002/0115982 | A1 | 8/2002 | Barbut et al. |
| 2005/0059930 | A1 | 3/2005 | Garrison et al. |
| 2005/0059931 | A1 | 3/2005 | Garrison et al. |
| 2005/0149112 | A1 | 7/2005 | Barbut |
| 2006/0009798 | A1 | 1/2006 | Callister et al. |
| 2006/0149393 | A1 | 7/2006 | Calderon |
| 2006/0200075 | A1 | 9/2006 | Zadno-Azizi |
| 2007/0010782 | A1 | 1/2007 | Doty et al. |
| 2007/0055132 | A1 | 3/2007 | Camus et al. |
| 2008/0058759 | A1 | 3/2008 | Makower et al. |
| 2008/0269718 | A1 | 10/2008 | Wiener et al. |
| 2009/0018526 | A1 | 1/2009 | Power et al. |
| 2009/0043194 | A1 | 2/2009 | Barbut |
| 2009/0048577 | A1 | 2/2009 | Gillies et al. |
| 2009/0088676 | A1 | 4/2009 | Murata |
| 2009/0131866 | A1 | 5/2009 | Zhang et al. |
| 2009/0198093 | A1* | 8/2009 | Meissner ............... A61N 7/02 600/2 |
| 2009/0264819 | A1 | 10/2009 | Diethrich et al. |
| 2009/0275918 | A1 | 11/2009 | Crocker |
| 2010/0016836 | A1 | 1/2010 | Makower et al. |
| 2010/0106181 | A1 | 4/2010 | Gross et al. |
| 2011/0093000 | A1 | 4/2011 | Ogle et al. |
| 2011/0152683 | A1 | 6/2011 | Gerrans et al. |
| 2011/0218494 | A1 | 9/2011 | Gerrans et al. |
| 2011/0257577 | A1 | 10/2011 | Lane et al. |
| 2011/0282195 | A1 | 11/2011 | Solar et al. |
| 2011/0295114 | A1 | 12/2011 | Agah et al. |
| 2012/0259215 | A1 | 10/2012 | Gerrans et al. |
| 2014/0214002 | A1 | 7/2014 | Lieber et al. |
| 2014/0276135 | A1* | 9/2014 | Agah ................... A61M 5/142 600/485 |
| 2014/0364835 | A1* | 12/2014 | Allen ............... A61M 25/0068 604/509 |
| 2016/0015948 | A1 | 1/2016 | Agah et al. |
| 2016/0082178 | A1 | 3/2016 | Agah et al. |
| 2017/0056629 | A1 | 3/2017 | Agah et al. |
| 2017/0157370 | A1 | 6/2017 | Agah et al. |
| 2018/0169067 | A1 | 6/2018 | Bascomb et al. |

FOREIGN PATENT DOCUMENTS

| | | |
|---|---|---|
| WO | WO 89/07413 | 8/1989 |
| WO | WO 01/70325 | 9/2001 |
| WO | WO 02/074178 | 9/2002 |
| WO | WO 2011/068946 A1 | 6/2011 |
| WO | WO 2014/197362 A1 | 12/2014 |
| WO | WO 2016/011328 A1 | 1/2016 |

OTHER PUBLICATIONS

Gastrointestinal Tumor Study Group. Further evidence of effective adjuvant combined radiation and chemotherapy following curative resection of pancreatic cancer. Cancer 59: 2006-2010, 1987 (Year: 1987).*

Neoptolemos JP et al. Adjuvant chemoradiotherapy and chemotherapy in resectable pancreatic cancer: a randomised controlled trial. The Lancet 358: 1576-1585, Nov. 10, 2001 (Year: 2001).*

Wasan HS. The emerging synergy between radioembolization, systemic chemotherapy, and liver surgery in metastatic colorectal cancer. European Oncological Disease, 2007;1(1):53-8) (Year: 2007).*

Multhoff G and Vaupel P. Radiation-induced changes in microcirculation and interstitial fluid pressure affecting delivery of macromolecules and nanotherapeutics to tumors. Frontiers in Oncology, 2012; 2: 1-6, (Year: 2012).*

European Search Report for European Application No. 10835110.7, dated Mar. 21, 2013, 10 pages.

Office Action for European Application No. 10835110.7, dated Jun. 1, 2015, 7 pages.

Office Action for U.S. Appl. No. 12/958,711, dated Aug. 20, 2013, 23 pages.

Office Action for U.S. Appl. No. 12/958,711, dated Mar. 7, 2014, 14 pages.

International Search Report and Written Opinion for International Application No. PCT/US2010/058684, dated Feb. 17, 2011, 11 pages.

Office Action for U.S. Appl. No. 14/293,603, dated Dec. 15, 2015, 14 pages.

Office Action for U.S. Appl. No. 14/293,603, dated May 10, 2016, 17 pages.

International Search Report and Written Opinion for International Application No. PCT/US2014/040485 dated Nov. 3, 2014, 12 pages.

Office Action for U.S. Appl. No. 14/870,833, dated Dec. 14, 2015, 10 pages.

Office Action for U.S. Appl. No. 14/870,833, dated May 9, 2016, 11 pages.

Office Action for U.S. Appl. No. 14/968,415 dated Mar. 2, 2016, 13 pages.

Office Action for U.S. Appl. No. 14/958,428, dated Apr. 6, 2016, 19 pages.

Communication Pursuant to Article 94(3) EPC issued by the European Patent Office for Application No. 10835110.7, dated Jan. 1, 2017, 5 pages.

Office Action issued by The United States Patent and Trademark Office for U.S. Appl. No. 14/958,428, dated Sep. 1, 2016, 20 pages.

Office Action issued by The United States Patent and Trademark Office for U.S. Appl. No. 14/958,428, dated Apr. 20, 2017, 14 pages.

Office Action issued by the Indian Patent Office for Application No. 1632/MUMNP/2012, dated Jul. 26, 2018, 6 pages including English translation.

International Search Report and Written Opinion issued by the International Searching Authority for Application No. PCT/US2018/033482, dated Aug. 24, 2018 14 pages.

Anonymous: Researchers Report Survival Benefits with Use of RenovoCathTM in Patients with Locally Advanced Pancreatic Tumors, Renovo Rx (Apr. 19, 2017), Retrieved from the Internet: URL:http://renovorx.com/researchers-report-survival-benefits-use-renovocath-patients-locally-advanced-pancreatic-tumors/ [retrieved on Jul. 24, 2018], 2 pages.

Mahadevan et al., "Stereotactic Body Radiotherapy and Gemcitabine for Locally Advanced Pancreatic Cancer," Int. J. Radiation Oncology Biol. Phys. 78(3):735-742 (2010).

RenovoRx: "RenovoCath Animation", Dec. 17, 2014 (Dec. 17, 2014), Retrieved from the Internet: URL:https://www.youtube.com/watch?v=LFZ7tv Cu2a4&feature=youtu.be [retrieved on Aug. 7, 2018], 1 page.

Anonymous: "RenovoCath for Targeted Fluid Delivery Into Peripheral Vasculature Cleared in Europe", Medgadget Oct. 23, 2015 (Oct. 23, 2015), Retrieved from the Internet: URL:https://www.medgadget.com/2015/10/renovocath-targeted-fluid-delivery-peripheral vasculature-cleared-europe.html [retrieved on Jul. 25, 2018], 2 pages.

Final Office Action issued by The United States Patent and Trademark Office for U.S. Appl. No. 14/958,428, dated Jan. 22, 2018, 35 pages.

Examination Report issued by the European Patent Office for Application No. 10835110.7, dated Apr. 25, 2018, 4 pages.

America Cancer Society; Cancer facts and figures, American Cancer Society; 72 pages; retireved from the internet (https://www.cancer.org/research/cancer-facts-statistics/all-cancer-facts-figures/cancer-facts-figures-2016.html); (year of pub. sufficiently earlier than effective US filing date and any foreign priority date) 2016.

Burkhardt et al; Intra-arterial chemotherapy for malignant gliomas: a critical analysis; Interventional Neuroradiology; 17(3); pp. 286-295; Sep. 2011.

cancer.net; Colorectal cancer: stages; 12 pages; retrieved from the internet (https://www.cancer.net/cancer-types/colorectal-cancer/stages) on Jan. 14, 2020.

cancer.net; Liver cancer: statistics; 2 pages; retrieved from the internet (https://www.cancer.net/cancer-types/liver-cancer/statistics) on Jan. 14, 2020.

(56) References Cited

OTHER PUBLICATIONS cancer.net; Uterine cancer: Statistics; 2 pages; retrieved from the internet (https://www.cancer.net/cancer-types/uterine-cancer/statistics) on Jan. 14, 2020.

Chauffert et al., Phase III trial comparing intensive induction chemoradiotherapy (60 Gy, infusional 5-FU and intermittent cisplatin) followed by maintenance gemcitabine with gemcitabine alone for locally advanced unresectable pancrreatic cancer. Definitive results of the 2000-01 FFCD?SFRO study; Annals of Oncology: 19(9); pp. 1592-1599; Sep. 2008.

Kawaguchi et al: Comparison of neoadjuvant intraaterial chemotherapy versus concurrent chemoradiotherapy in patients with stage IIB uterine cervical cancer; World Journal of Oncology: 4(6); pp. 221-229; Dec. 2013.

Lewandowski et al.; Transcatheter intraarterial therapies: rationale and overview; Radiology; 259(3); pp, 641-657; Jun. 2011.

National Cancer Institute; About cancer; 3 pages; retrieved from the internet (https://www.cancer.gov/about-cancer) on Jan. 14, 2020.

Sante; Lungcancer prognosis; 3 pages; retrieved from the internet (https://translate.google.com/translate?hl=en&sl=ft&u=http://www.lungcancer-prognosis.com/&prev=search) on Jan. 14, 2020.

Suryadevra et al; Immunotherapy for malignant glioma; Surgical Neurology International; 6(Suppl 1); S68-S77; Feb. 2015.

Vogl et al.; Regional chemotherapy of the lung; transpulmonary chemoembolization in malignant lung tumors; Seminars in Interventional Radiology; 30(2); pp. 176-184; Jun. 2013.

Agah et al.; U.S. Appl. No. 16/685,950 entitled "Methods for delivery of therapeutic materials to treat pancreatic cancer," filed Nov. 15, 2019.

Agah et al.; U.S. Appl. No. 16/685,974 entitled "Methods for treating cancerous tumors," filed Nov. 15, 2019.

\* cited by examiner

1100

METHODS FOR TREATING CANCEROUS TUMORS

CROSS REFERENCE TO RELATED APPLICATIONS

This application claims priority to and the benefit of U.S. Provisional Patent Application No. 62/507,962, titled "Methods for Treating Cancerous Tumors," filed May 18, 2017, the disclosure of which is incorporated herein by reference in its entirety.

BACKGROUND

Cancer begins when a cell begins dividing uncontrollably. Eventually, these cells form a visible mass or tumor. Solid tumors are masses of abnormal tissue that originate in organs or soft tissues that typically do not include fluid areas. Some examples of solid tumors include: pancreatic cancer, lung cancer, brain cancer, liver cancer, uterine cancer, and colon cancer.

Traditionally, tumors have been treated with surgical resection, radiation, and/or chemotherapy. Surgical resection involves the removal of tumor tissue. Radiation uses beams of intense energy to kill cancer cells and to shrink tumors. And chemotherapy involves the use of therapeutic agents or drugs to treat cancer. But surgical resection may not completely remove a tumor. Radiation and chemotherapy can have undesirable systemic side effects, including extreme fatigue, hair loss, infection, nausea and vomiting, and others that limit their usefulness. More recently, direct activation of the patient's immune system to attack cancerous cells has shown promise in treating certain solid tumors, but not all. Thus, the need for an improvement in both the safety and the efficacy of current therapy still exists.

Use of localized intra-arterial therapies, including trans-arterial chemo-delivery (TAC) or trans-arterial chemo-embolization (TACE), has been shown to be clinically beneficial for a certain subset of solid tumors. TAC or TACE can involve imaging an organ having a tumor using angiography, isolating a branch of the artery that feeds the tumor or portion of the organ containing the tumor, and then locally injecting chemotherapy in a bolus fashion via the isolated artery. Localized intra-arterial therapies allow higher drug concentration to reach the tumor, overcoming the problem of poor blood flow to tumor mass in comparison to healthy tissue. Furthermore, localized intra-arterial therapies can also take advantage of the first pass effect of chemotherapeutics by generating higher level drug concentrations at the tumor cell membrane and therefore enhancing cellular drug uptake as compared to non-localized infusion. Lastly, local delivery can reduce systemic side effects of chemotherapy.

One of the limitations of TAC and TACE is the need for selective cannulation and isolation of the tumor feeder vessel or arterial branch that can target the smallest portion of the organ containing the tumor. But it may be difficult to target and limit drug delivery to a small portion of the organ containing the tumor while achieving desired efficacy levels with the cancer treatment. On the one hand, limiting drug delivery to a small portion of the organ can reduce the potential impact of the administered drug on surrounding healthy tissue. But on the other hand, when the isolated region becomes too small, drug uptake levels by the tumor may decrease and reduce the efficacy of the cancer treatment. Given these limitations, a method to deliver a sufficient dose of a chemotherapeutic drug in addition to and independent of the need to cannulate and isolate to a specific feeding/supplying branch of a tumor feeder vessel is highly desirable.

Pancreatic Cancer

In 2016, pancreatic cancer ranked as the fourth leading cause of cancer death in the United States, and the tenth most commonly diagnosed tumor type in men and women. Estimates of incidence and deaths caused by pancreatic cancer are approximately 53,070 and 41,780, respectively (American Cancer Society: Cancer Facts and Figures, American Cancer Society, 2016). Projections based on the changing demographics of the United States population and changes in incidence and death rates reveal that, unless earlier diagnosis is made possible or better treatment options become available, pancreatic cancer is anticipated to move from the fourth to the second leading cause of cancer death in the United States by 2020.

Systemic chemotherapy as treatment for pancreatic cancer may be modestly effective due to low drug penetration in the pancreas because a drug infused systemically only moderately penetrates the pancreas, which may generally increase toxicity within a patient's body but not have an effect on the cancer. In many instances, tumors located in the pancreas are located in tissue surrounding an artery but not in a region of an artery that can be targeted and isolated. Accordingly, it may be difficult for a biologic agent or drug to reach and treat the tumors. Among solid tumors, drug delivery to pancreatic tumors is especially difficult due to the hypo-vascular and poorly perfused nature of the pancreas. The unique environment of the pancreas lends itself to reduced drug levels within the organ tissue, which reduces the effectiveness of systemic chemotherapy that relies on a functional vasculature for delivery to tumor cells. Also, the effect of chemotherapy is concentration dependent, and systemic infusion oftentimes results in low concentrations. Aside from dosing limitations in treating pancreatic cancer, many systemic side effects of chemotherapeutic agents can result from the treatment.

In an attempt to increase the effectiveness of chemotherapeutic agents on pancreatic tumors while decreasing systemic toxicity, various researchers have delivered drugs directly to the pancreas using traditional endovascular catheters. These initial attempts have been limited due to the redundant nature of blood supply to the pancreas and its adjacent organs. Non-selective engagement of the pancreatic vessels can also lead to the wash through of chemotherapy to other adjacent organs. Most of the arterial branches to the pancreas are small; thus, selective engagement of these small branches via conventional catheters is difficult. Thus, there is a need to address these and other deficiencies.

Lung Cancer

Lung cancer is another deadly cancer that is difficult to treat. Lung cancer is responsible for 23% of total cancer deaths. Long-term exposure to tobacco smoke causes 80 to 90% of lung cancers. Nonsmokers account for 10 to 15% of lung cancer cases, and these cases are often attributed to a combination of genetic factors or other environmental exposures (Vogl, T. J., et al., Seminars in Interventional Radiology, 2013, 30(2): 176-184).

Common treatments for lung cancer depend on the cancer's specific pathology, staging, and the patient's performance status (e.g., ability to breath). Traditional treatment options are surgery, chemotherapy, immunotherapy, radiation therapy, and palliative care. Intravascular techniques for localized delivery of chemotherapeutic agents have also been used to treat lung cancer, and include cancer therapy such as arterial chemoembolization, bronchial artery infusion (BAI), isolated lung perfusion (ILP), and lung suffusion. Chemotherapeutics approved for the treatment of non-small cell lung cancer in the United States include methotrexate, paclitaxel albumin-stabilized nanoparticle formulation, afatinib dimaleate, everolimus, alectinib, pemetrexed di sodium, atezolizumab, bevacizumab, carboplatin, ceritinib, crizotinib, ramucirumab, docetaxel, erlotinib hydrochloride, gefitinib, afatinib dimaleate, gemcitabine hydrochloride, pembrolizumab, mechlorethamine hydrochloride, methotrexate, vinorelbine tartrate, necitumumab, nivolumab, paclitaxel, ramucirumab, and osimertinib, and the combinations carboplatin-taxol and gemcitabine-ci splatin (https://www.cancer.gov/aboutcancer). Drugs approved for the treatment of small cell lung cancer include methotrexate, everolimus, doxorubicin hydrochloride, etoposide phosphate, topotecan hydrochloride, mechlorethamine hydrochloride, and topotecan (https://www.cancer.gov/aboutcancer). Lung cancer such as small cell lung cancer can sometimes be treated with a combination of radiation therapy and one or more chemotherapeutics. But other types of lung cancer such as non-small cell lung cancer may not be sensitive to current chemotherapeutics. In many instances, current treatment methods are not effective at providing meaningful treatment or palliative care. Thus, it is desirable to have a more effective method for treating lung cancer tumors.

Brain Cancer

Malignant gliomas comprise up to 80% of primary malignant brain tumors in the adults. Among these, glioblastomas are the most deadly and account for 82% of all malignant gliomas (Suryadevra, C. M., et al., *Surg. Neurol. Int.*, 2015, 6(1):S68-S77). The current standard of care includes surgical resection, followed by adjuvant external beam radiation and chemotherapy with drugs such as temozolomide. Conventional therapy is nonspecific and often results in a tragic destruction of healthy brain tissue. These treatments can be incapacitating and produce a median overall survival of just twelve to fifteen months. In addition, the invasive properties of glioblastomas make complete resection difficult and the glioblastomas may recur following initial treatment. Malignant gliomas are also highly vascularized tumors, and their unique capacities for regulating angiogenesis contribute to their resistance against known therapies.

Malignant gliomas, including glioblastoma multiforme, have been treated with inter-arterial chemotherapy. Typically, a catheter is inserted in the femoral artery and ends in the carotid artery, while a separate microcatheter is also inserted into the femoral artery and used to explore the specific vessels feeding the tumor for administration of the chemotherapy (Burkhardt, J-K., et al., *Interventional Radiology*, 2011, 17:286-295). But such methods are not always effective and can be improved.

Liver Cancer

Liver cancer is another difficult-to-treat cancer characterized by solid tumors. In 2016, an estimated 39,230 adults (28,410 men and 10,820 women) in the United States will be diagnosed with primary liver cancer. Liver cancer also commonly metastasizes to other parts of the body. It is estimated that 27,170 deaths (18,280 men and 8,890 women) from this disease will occur this year. Liver cancer is the tenth most common cancer and the fifth most common cause of cancer death among men. It is also the eighth most common cause of cancer death among women (American Cancer Society: Cancer Facts and Figures, American Cancer Society, 2016). When compared with the United States, liver cancer is much more common in developing countries within Africa and East Asia. In some countries, it is the most common cancer type. The one-year survival rate for people with liver cancer is 44%. The five-year survival rate is 17%. For the 43% of people who are diagnosed at an early stage, the five-year survival rate is 31%, while it is only 11% if the cancer has spread to surrounding tissues or organs and/or the regional lymph nodes. If the cancer has spread to a distant part of the body, the 5-year survival rate is only 3% (http://www.cancer.net/cancer-types/liver-cancer/statistics).

Currently, patients with hepatocellular carcinoma and cirrhosis are frequently treated with non-specific trans-arterial therapy using techniques that deliver treatments directly into the liver (Lewandowski, R. J., et al., *Radiology*, 2011, 259(3):641-657). Physicians use the femoral artery to gain access to the hepatic artery, one of two blood vessels that feed the liver. Trans-arterial therapy such as TACE involves delivery of chemotherapy directly to the liver, followed by a process to embolize the chemotherapy. In this therapy, a thick, oily substance (for example, Lipiodol) is mixed with chemotherapy (for example, floxuridine, sorafenib tosylate or a mixture of platinol, mitomycin, and adriamycin) and injected under radiological guidance directly into the artery supplying the tumor via a catheter. The Lipiodol, or other particles, helps to contain the chemotherapy within the tumor and blocks further blood flow, thus cutting off the tumor's food and oxygen supply. TACE with doxorubicin-filled beads delivers the beads directly to the liver, which releases chemotherapy slowly over time and also blocks the blood flow to the tumor. In a similar therapy, radioactive yttrium beads are delivered via a catheter into the hepatic artery. The beads deliver radiation to the tumor, which kills the tumor cells, although other unintended areas of the liver may also receive radiation, creating undesirable destruction of healthy tissue. Thus, there is a need to improve current treatment methods.

Uterine Cancer

In 2016, an estimated 60,050 women in the United States were diagnosed with uterine endometrial cancer, with an estimated 10,470 deaths occurring (http://www.cancer.net/cancer-types/uterine-cancer/statistics). Uterine cancer is the fourth most common cancer for women in the United States. The incidence of endometrial cancer is rising, mainly due to a rise in obesity, which is an important risk factor for this disease. It is the sixth most common cause of cancer death among women in the United States with the 5-year survival rate being 82%.

Concurrent chemoradiotherapy (CCRT) is the main treatment for locally advanced cervical cancer. Neoadjuvant chemotherapy (NAC) was widely employed until CCRT became the standard, and conflicting results have been reported. Neoadjuvant intra-arterial chemotherapy (IANAC) is another method for delivering NAC as an alternative to systemic chemotherapy. IANAC has been reported to achieve beneficial results that cannot be obtained by systemic chemotherapy or CCRT. Kawaguchi et al. have reported that IANAC with cisplatin followed by radical hysterectomy or radiotherapy afforded similar results to concurrent chemoradiotherapy for stage IIIB cervical cancer (Kawaguchi et al., *World Journal of Oncology*, 2013, 4(6): 221-229). Drugs approved for use in the United States for the treatment of cervical cancer include bevacizumab, bleomycin, and topotecan hydrochloride, and the combination gemcitabine-cisplatin. Uterine cancer of endometrial origin may be treated with, for example, megestrol acetate. But many systemic side effects of chemotherapeutic agents can result from current treatment methods. It is desirable to have a specific means of targeting uterine tumors.

Colon Cancer

In the United States, colorectal cancer is the fourth most common cancer diagnosed each year for all adults combined. Separately, it is the third most common cancer in men and third most common cancer in women. In 2016, an estimated 134,490 adults in the United States were diagnosed with colorectal cancer, with 95,270 new cases of colon cancer and 39,220 new cases of rectal cancer. It is estimated that 49,190 deaths (26,020 men and 23,170 women) were attributed to colon or rectal cancer in 2016. Colorectal cancer is the second leading cause of cancer death in the United States, although when it is detected early, it can often be cured. The death rate from this type of cancer has been declining since the mid-1980s, probably because of an improvement in early diagnosis. The 5-year survival rate colorectal cancer is 65%, while the 10-year survival rate is 58% (http://www.cancer.net/node/18707).

When possible, surgical removal of colorectal tumors is the treatment of choice as it can eliminate the cancer completely. However, metastasis to other organs, particularly the liver and the lung, is common and complicates the treatment of colon and rectal cancer dramatically. It is therefore desirable to have a method of treating metastasized colon and rectal cancers that are present in other organs of the body. Drugs approved for use in treating colon cancer in the United States include bevacizumab, irinotecan hydrochloride, capecitabine, cetuximab, ramucirumab, oxaliplatin, 5-FU, fluorouracil, leucovorin calcium, trifluridine, tipiracil hydrochloride, oxaliplatin, panitumumab, ramucirumab, regorafenib, ziv-aflibercept and the combinations capox, folfiri-bevacizumab, folfiri-cetuximab, FU-LV, xeliri and xelox.

SUMMARY OF THE INVENTION

Apparatuses and methods are described herein that relate to, for example, the treatment of cancerous tumors. In some embodiments, the method comprises: a) first administering a course of radiation therapy targeting an area including a solid tumor; b) second waiting a period of time for the radiation to take effect on the vasculature in the area; and c) third administering a therapeutically effective dose of a chemotherapeutic agent to an isolated arterial section near the solid tumor.

In some embodiments, the method comprises: a) first administering a targeted dose of radiation to an area including a solid tumor; b) second waiting a period of time; c) third isolating an area containing a cancerous tumor by, for example, isolating an arterial segment proximate to the tumor; and d) fourth administering a localized therapeutically effective dose of a chemotherapeutic agent.

In some embodiments, the method comprises: a) administering a course of radiation therapy to an area including a solid tumor; b) isolating the proximal and the distal part of the vasculature closest to the tumor to produce an isolated arterial segment; c) decreasing the intraluminal pressure of the isolated arterial segment to the level of the interstitium; and d) administering a therapeutically effective dose of a chemotherapeutic drug. In one embodiment, the method comprises an additional step of waiting a period of time following the step of administering the course of radiation therapy.

In some embodiments, the method includes delivering radiation therapy to a target area including a tumor; and inserting a catheter device into an artery where the catheter device includes a first occlusion member, a second occlusion member, and a body defining a lumen in fluid communication with an infusion port. The infusion port is disposed between the first occlusion member and the second occlusion member. The first occlusion member and the second occlusion member are moved to an area of the artery disposed proximate to the target area. The first occlusion member and the second occlusion member are deployed to isolate the area of the artery disposed proximate to the target area. A dose of chemotherapeutic agent is then delivered to the isolated area of the artery via the lumen and the infusion port. The chemotherapeutic agent permeates to the target area including the tumor from the isolated area of the artery.

In some embodiments, the method includes administering a dose of radiation to a target area including a tumor; inserting a catheter device into a vessel, the catheter device including a first occlusion element and a second occlusion element; isolating a segment of the vessel proximate to the target area using the first occlusion element and the second occlusion element; and delivering a dose of an agent to the segment via the catheter device.

In some embodiments, the method includes administering a dose of radiation to a target area including a tumor; isolating a segment of the vessel proximate to the target area; adjusting an intraluminal pressure of the segment to a level of pressure of an interstitial space between the vessel and the target area; and delivering a dose of an agent to the segment via the catheter device.

Other objects of the invention may be apparent to one skilled in the art upon reading the following specification and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
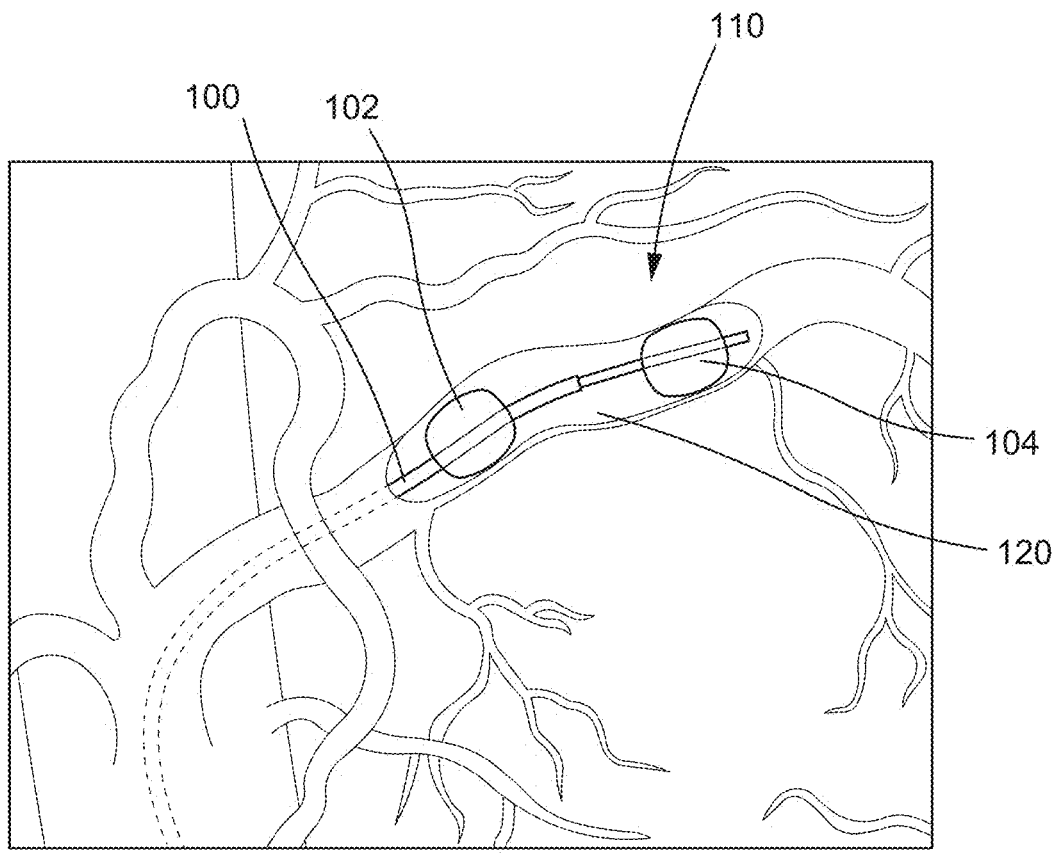
FIG. 1 is an illustration of a catheter device disposed within a vessel, according to an embodiment.

This application is not limited to particular methodologies or the specific compositions described. It is also understood that the terminology used herein is for the purpose of describing particular embodiments only, and is not intended to be limiting, since the scope of the present application will be limited only by the appended claims and their equivalents.

Unless defined otherwise, technical and scientific terms used herein have the same meaning as commonly understood by one of ordinary skill in the art to which this invention belongs. Although any methods and materials similar or equivalent to those described herein can be used in the practice or testing of the present application, the preferred methods and materials are now described.

As used herein and in the appended claims, the singular forms "a," "and," and "the," include plural referents unless the context clearly dictates otherwise. Thus, for example, the term "chemotherapeutic" is intended to mean a single chemotherapeutic or a combination of chemotherapeutics; "a course of radiation therapy" is intended to mean one or more courses of radiation therapies, or combinations thereof; the term "agent" is intended to mean a single agent or a combination of agents, and so on and so forth.

As utilized in accordance with the present disclosure, the following terms, unless otherwise indicated, shall be understood to have the following meanings:

The words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the implant end first inserted inside the patient's body would be the distal end of the implant, while the implant end to last enter the patient's body would be the proximal end of the implant.

"Treat", "treating" and "treatment" of cancerous tumors refer to reducing the frequency of symptoms of cancer (including eliminating them entirely), avoiding the occurrence of cancer, and/or reducing the severity of symptoms of cancer.

"Therapeutically effective amount" and "therapeutically effective dose" means the amount or dosage of a compound that, when administered to a patient for treating cancerous tumors, is sufficient to effect such treatment. The "therapeutically effective amount" or "therapeutically effective dose" will vary depending on, for example, the compound, the size of the tumor, and the age, weight, etc., of the patient to be treated.

OVERVIEW OF THE INVENTION

The present application provides a method for treating or ameliorating solid cancerous tumors, wherein a course of targeted radiation therapy is first administered to an area including one or more tumors. A period of time is allowed to elapse in order for the radiation to take effect in downsizing the tumor(s). The radiation may also reduce the microvasculature in the tissue in the area including the tumor(s). This period is followed by the administration of a therapeutically effective amount of a chemotherapeutic agent to an isolated arterial section near the solid tumor. Isolation of the arterial section may be accomplished by isolating the proximal and the distal part of the vasculature closest to the tumor whereby the intraluminal pressure is then decreased to the level of the interstitium. The therapeutically effective dose of the chemotherapeutic agent may then be administered via infusion. Combination of radiation therapy followed by properly administered chemotherapy is complementary and has a synergistic clinical effect when combined.

Intra-arterial delivery of chemotherapy, including TAC and TACE, has been shown to be effective and safe in treatment of certain solid tumors. A prerequisite for effective TAC or TACE is the selective engagement of nearby arterial vessels and, more commonly, the vessels feeding the tumor itself. The precise engagement of the feeding or branch vessel remains a major limitation for expanding the use of TACE and TAC in solid tumors, including but not limited to, pancreatic adenocarcinoma. The isolation of the artery supplying the tumor or the relevant tissue can be a technical challenge for a number of reasons, for example: a) there are organs with no dedicated single blood vessel supplying those specific organs; b) side and terminal branches of an artery can cause collateral flow to tissues and organs beyond the area of interest; and c) the tumor feeder vessels may be too small for detection by angiography; and d) the feeding branch/artery cannot be cannulated.

To address these problems, methods disclosed herein may involve administering radiation therapy to an area including a tumor. The radiation may reduce the microvasculature in the tissue in the area including the tumor. After the radiation therapy, the proximal and the distal part of the vasculature (e.g., an artery) closest to the tumor is isolated using a double balloon catheter. Both the side and the terminal branches are excluded, which prevents drug washout. The reduced microvasculature in the tissue in the area also reduces drug washout. Upon inflation of both balloons in the isolated arterial segment, the intra-luminal pressure is reduced to the level of interstitium (typically, 10-20 mmHg). A therapeutic agent such as, for example, a chemotherapeutic drug, can be infused into the isolated arterial segment. The infusion of the chemotherapeutic drug in the isolated region, without any major runoff, leads to an increase in the intra-luminal pressure of at least about 30 mmHg in the isolated vessel segment. The pressure gradient forces the infused agent to traverse the arterial wall and enter the surrounding tissue, especially the vasa vasorum surrounding the vessel wall, with subsequent influx of the therapeutic agent into the tissue. This technique is referred to herein as "trans-arterial micro-perfusion" or TAMP.

According to certain embodiments described herein, TAMP is not dependent on angiographic identification and cannulization of the tumor arterial supply or feeding vessels and thus overcomes deficiencies of current techniques. In TAMP, the drug traverses the arterial wall (e.g., endothelium and media) before entering into the adventitia and interstitium. The interstitial concentration achieved is dependent on both the influx of the drug into the tissue across the artery wall and the efflux of the drug out of the interstitium via capillaries in the tissue area and the venous system. Hence, one can increase localized tissue concentration by both increasing the influx and reducing the efflux using the approach described above. The infusion parameters that determine the influx of the drug via TAMP include, but are not limited to, the intraluminal pressure achieved between the balloons, the intraluminal drug concentration, and the duration of infusion. By varying these parameters, one can change the drug influx and interstitial concentration.

In some embodiments, catheter devices such as those described in U.S. patent application Ser. No. 14/293,603, filed Jun. 2, 2014, titled "Devices, methods and kits for delivery of therapeutic materials to a target artery," now issued as U.S. Pat. No. 9,457,171, and U.S. patent application Ser. No. 14/958,428, filed Dec. 3, 2015, titled "Occlusion catheter system and methods of use," the disclosures of which are incorporated herein by reference, can be used and/or adapted for use with TAMP techniques described herein. FIG. 1 depicts an example catheter device 100. The catheter device 100 includes a first occlusion element 102 and a second occlusion element 104. The occlusion elements 102, 104 can be any suitable devices or mechanisms that are configured to selectively limit, block, obstruct, or otherwise occlude a bodily lumen (e.g., artery) in which the occlusion elements 102, 104 are disposed. For example, in some embodiments, the occlusion elements 102, 104 can be inflatable balloons or the like that can be transitioned between a collapsed (e.g., deflated) configuration and an expanded (e.g., inflated) configuration. The first occlusion element 102 can be coupled to a distal end portion of a first catheter, and the second occlusion element 104 can be coupled to the distal end portion of a second catheter. Alternatively, in some embodiments, the first occlusion element 102 and the second occlusion element 104 can be coupled to a single catheter at different points along the catheter. The catheter device 100 can be used to isolate a segment 120 of a bodily lumen (e.g., artery) within the space defined between the first occlusion element 102 and the second occlusion element 104. After the segment 120 is isolated, a procedure can be performed within the isolated segment 120 such as, for example, delivering a therapeutic agent to the isolated segment 120 and surrounding tissue 110.

Figure 2:
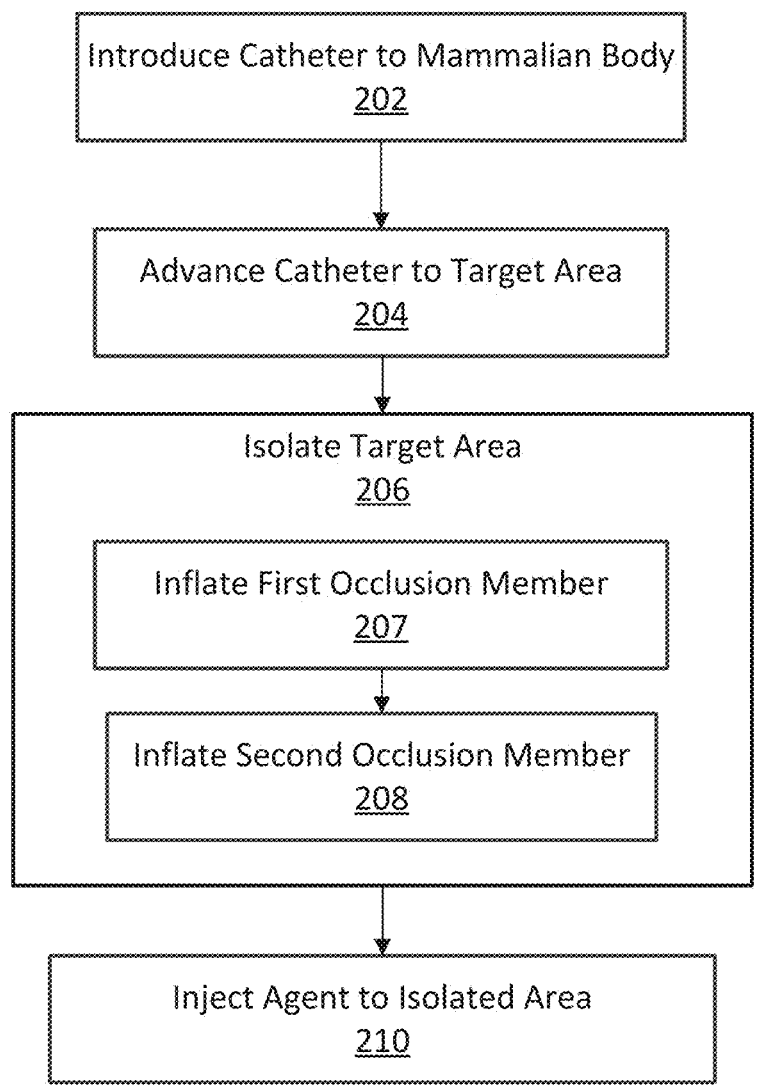
FIG. 2 is a flowchart illustrating a method for treating a cancerous tumor, according to embodiments described herein.

FIG. 2 illustrates a method 200 for performing a TAMP procedure. The method includes introducing a catheter (e.g., the catheter device 100) into a mammalian body into a bodily lumen (e.g., artery), at 202. The catheter can be advanced to a target area, at 204, and used to isolate the target area, at 206. In some embodiments, the catheter can include two occlusion members (e.g., occlusion elements 102, 104) that can be deployed (e.g., inflated) to isolate a segment of the bodily lumen to exclude the segment from its side and terminal branches. For example, a first occlusion member (e.g., a distal occlusion element) can be inflated, at 207, and a second occlusion member can be inflated (e.g., a proximal occlusion element), at 208. After the occlusion elements are deployed, an agent can be injected through an injection port of the catheter device to the isolated segment disposed between the two occlusion members, at 210. In some embodiments, a contrast dye can be can be injected into the isolated segment and the surrounding area can be visualized to determine whether the segment has been correctly isolated. For example, the injection of contrast through the infusion port can ensure that no extra vessels or bodily lumens are included in the isolated area. If desired, the catheter can be moved and the procedure repeated until the clinician can confirm that the catheter is correctly positioned. After the positioning of the catheter is confirmed, a therapeutic cell/biologic/agent can be introduced to the isolated segment through the infusion port.

Figure 3:
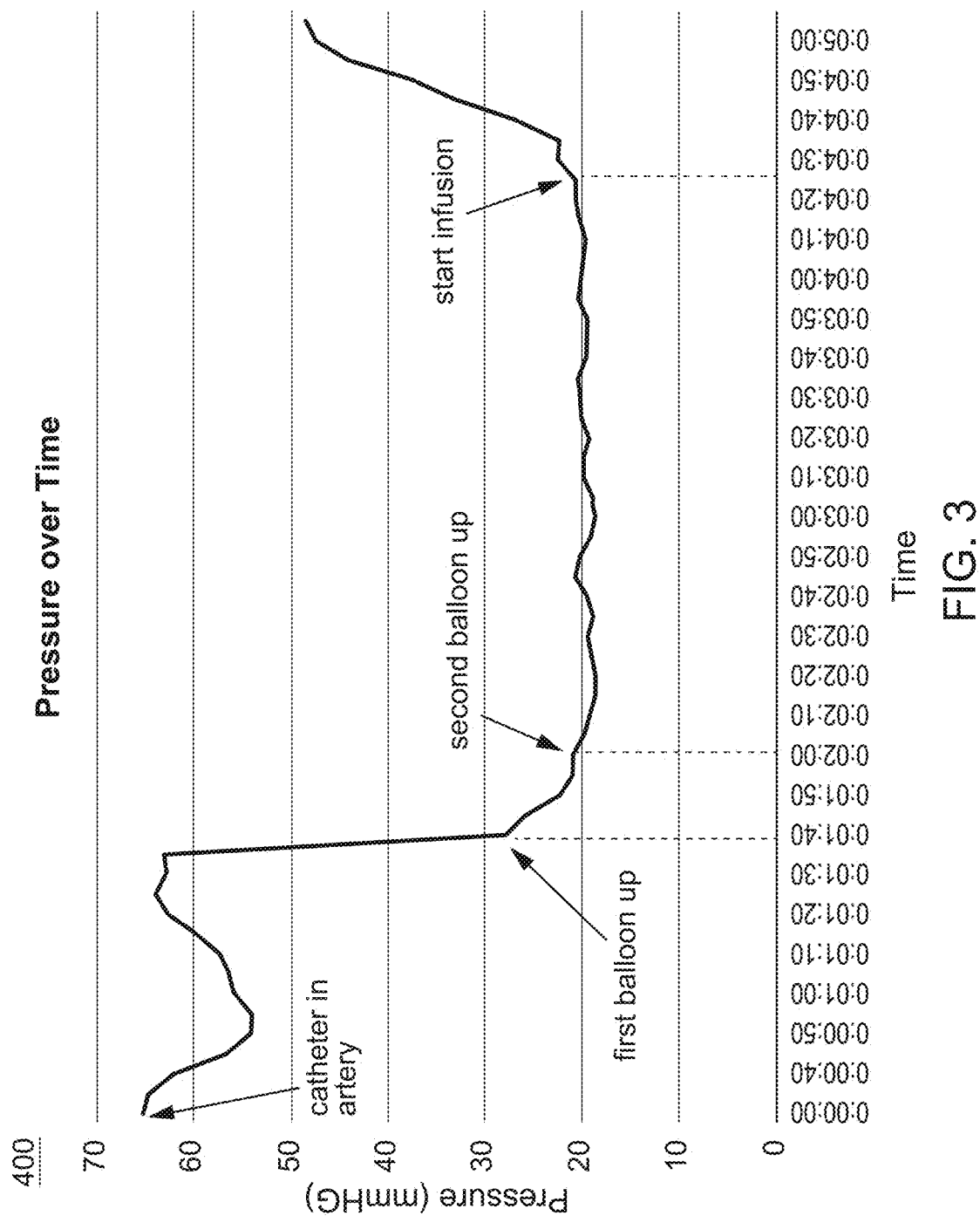
FIG. 3 is a graph showing a change in pressure (mmHg) in a vessel over time while undergoing treatment, according to an embodiment.

FIG. 3 graphically illustrates how pressure (mmHg) in a bodily lumen (e.g., artery) changes over time as a TAMP procedure is performed (e.g., method 200). As shown in FIG. 3, the pressure in the bodily lumen drops when a first balloon or occlusion element is inflated and continues to drop until a second balloon or occlusion element is inflated. The pressure then increases when an agent (e.g., a contrast dye, a therapeutic agent) is infused into the segment isolated by the first balloon and the second balloon.

Figure 4A:
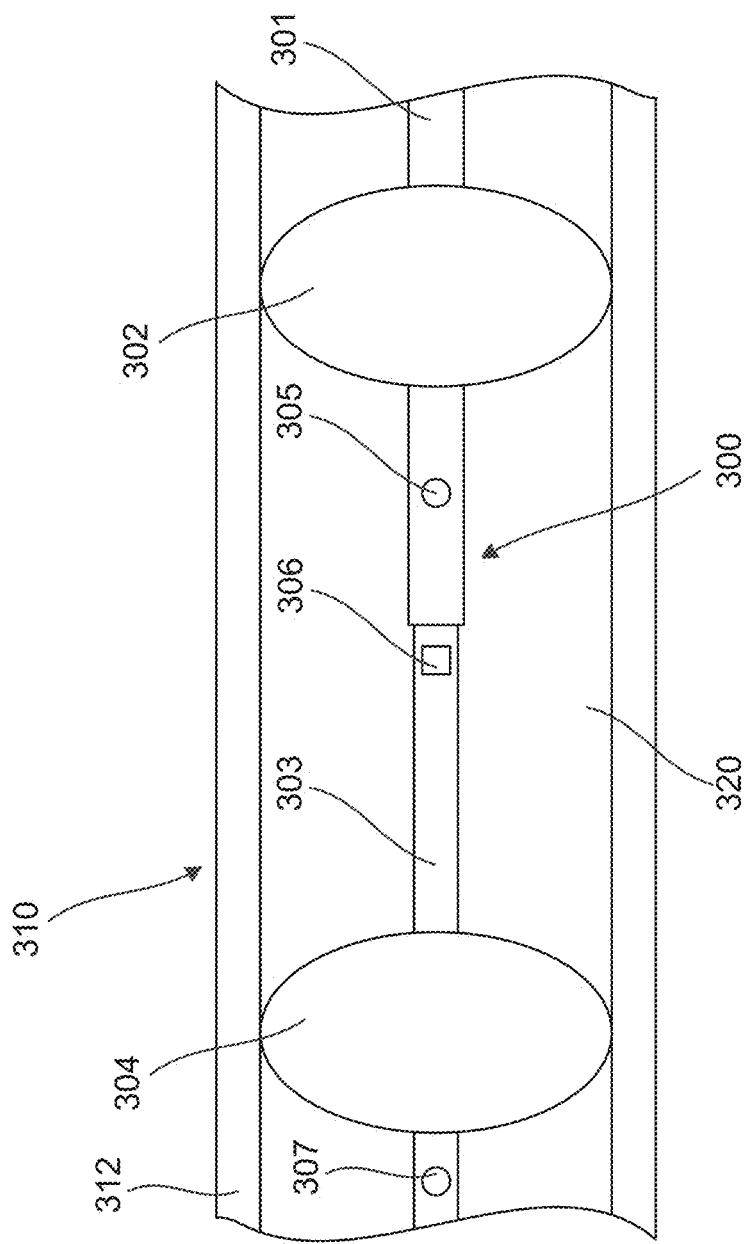
FIG. 4A is schematic illustration of a catheter device shown in a dilated configuration disposed within a vessel, according to an embodiment.
Figure 4B:
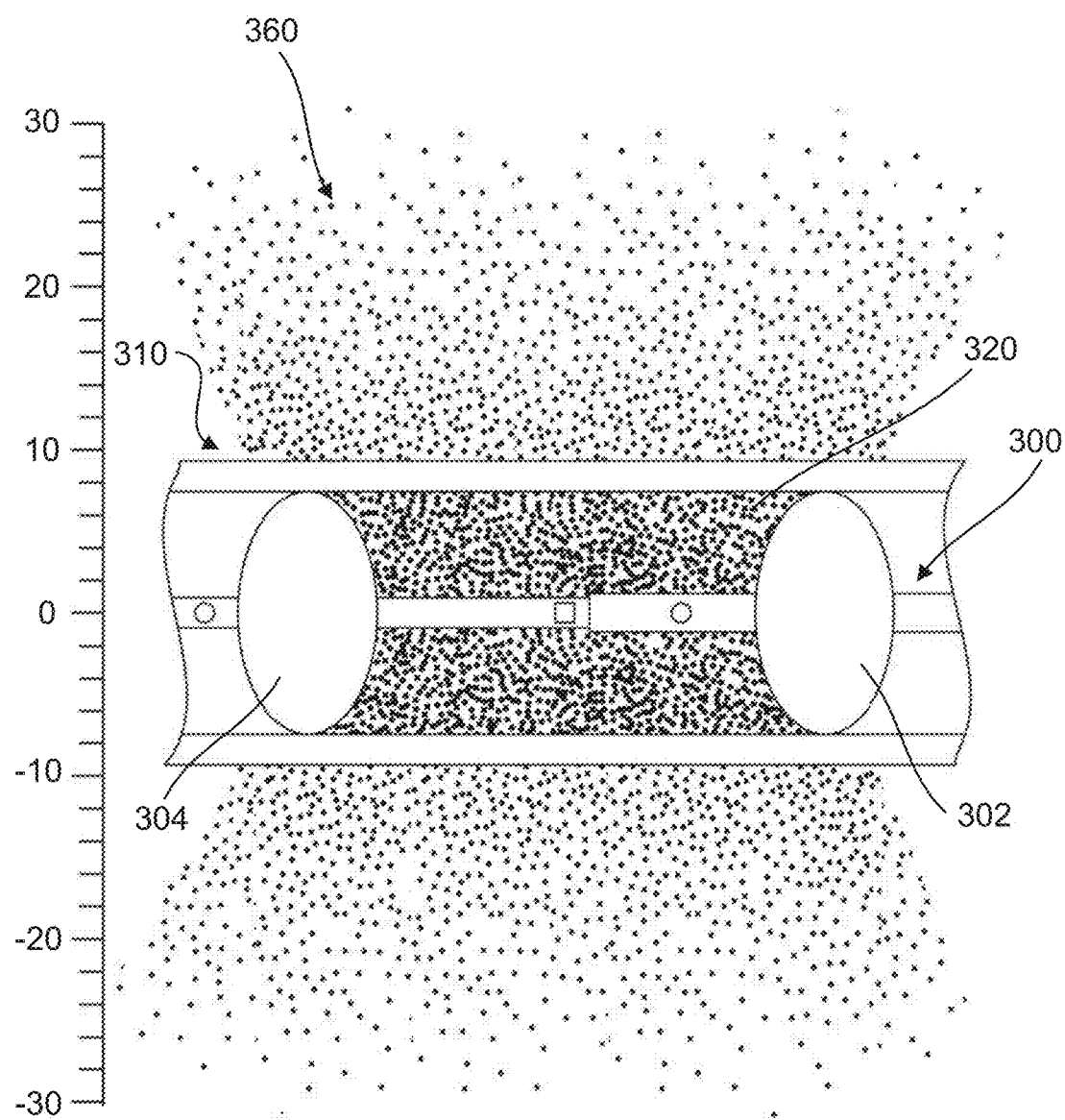
FIG. 4B is a schematic illustration of dispersal of an infused agent into tissue surrounding a vessel, according to an embodiment.

FIGS. 4A and 4B schematically depict an example of a catheter device 300 disposed within a bodily lumen 310 (e.g., artery) and the dispersal of an infused agent 360 through the bodily lumen 310 into surrounding tissue. According to methods described herein (e.g., method 200), the infused agent 360 can be injected into an isolated segment 320 and allowed to infuse into the surrounding tissue via, for example, a concentration gradient. As shown in FIG. 4B, the infused agent 360 can infuse through a wall 312 of the bodily lumen 310 into the surrounding tissue. As shown, the concentration of the agent 360 decreases as the distance (shown in millimeters (mm)) from the isolated segment 320 of the bodily lumen 310 increases.

In combination with the techniques described above, if one can decrease the tissue efflux of the chemotherapeutic drug, the drug concentration near an isolated segment of a bodily lumen may be advantageously increased. When a tumor is located in this region, the increased concentration can increase the effect of the chemotherapeutic drug on the tumor. One technique that can decrease tissue efflux is to radiate the tissue prior to treatment. Radiation can decrease tissue microvasculature in tissue containing cancerous tumors. Thus, combining prior radiation to decrease tissue microvasculature with TAMP can have a synergistic effect. Combining the steps of radiation of the cancerous tissue prior to the treatment, waiting two or more weeks for the microvasculature to decrease, followed by use of the TAMP technique to deliver chemotherapy in the isolated segment of the bodily lumen (e.g., artery) closest to the tumor, produces a synergistic effect that the use of the TAMP technique alone does not.

Methods described herein can be used to treat solid cancerous tumors arising from any organ of the body where the tumor has its own or a proximate blood supply provided by a bodily lumen (e.g., artery) that can be isolated. Examples of cancers that can be treated using methods described herein can be, but are not limited to, pancreatic cancer, lung cancer, liver cancer, uterine cancer, colon cancer, or brain cancer.

For example, apparatuses and methods described herein can be used to isolate a targeted region in a patient's pancreas. Studies have shown that a course of radiation prior to TAMP treatment has significant clinical benefit in patients with locally advanced pancreatic cancer. Combining these two modalities led to a significant increase in median survival, a reduction of tumor markers, and downsizing of the tumor. A similar combination therapy administered by methods described herein may have clinical benefit in solid tumors in other organs and tissue areas where TAMP may be considered as a treatment option. Such tumors include, but are not limited to, pancreatic tumors, lung tumors, brain tumors, liver tumors, uterine tumors, and colon tumors.

In some embodiments, a method of treating a cancerous tumor can involve: first administering a course of radiation therapy targeting tissue including a solid cancerous tumor; second waiting a period of time for the destructive effect of the radiation on the vasculature to take effect; and third administering a therapeutically effective dose of a chemotherapeutic agent to an isolated section of a bodily lumen near the solid tumor. The targeted solid tumor can be, for example, a pancreatic tumor, a lung tumor, a brain tumor, a liver tumor, a uterine tumor, or a colon tumor. The administration of radiation on the targeted tissue area can include, for example, delivering approximately 20 to 50 Gy of radiation over approximately one to five weeks in approximately one to 25 sessions. The period of time between administration of the radiation therapy and administration of the chemotherapeutic agent can be selected to maximize the devascularization of the tissue surrounding the tumor. Depending on various factors including the specific course of radiation and the specific tissue area or organ, this period of time can be, for example, approximately one to six months, as short as two weeks, or as long as six months. Examples of suitable chemotherapeutic agents include doxorubicin, erlotinib hydrochloride, everolimus, 5-FU, flurouracil, folfirinox, gemcitabine hydrochloride, gemcitabine-cisplatin, gemcitabine-oxaliplatin, irinotecan hydrochloride liposome, leucovorin, mitomycin C, mitozytrex, mutamycin, oxaliplatin, paclitaxel, paclitaxel albumin-stabilized nanoparticle formulation, or sunitinab malate or a combination of these drugs. In some embodiments, the section of the bodily lumen near the cancerous tumor can be isolated by the use of a catheter device to deliver the chemotherapeutic agent. In some embodiments, the catheter device can be used to increase the intraluminal pressure in the isolated section of the bodily lumen to achieve increased tissue penetration.

In some embodiments, a method of treating a cancerous tumor can involve: first administering a targeted dose of radiation to tissue including a solid tumor; second waiting a period of time; third isolating an area containing a cancerous tumor; and fourth administering a localized therapeutically effective dose of a chemotherapeutic agent. Similar to other methods described herein, the targeted solid tumor may be, for example, a pancreatic tumor, a lung tumor, a brain tumor, a liver tumor, a uterine tumor, or a colon tumor. The administration of radiation on the targeted tissue area can include, for example, delivering approximately 20 to 50 Gy of radiation over approximately one to five weeks in approximately one to 25 sessions. The period of time between administration of the radiation therapy and administration of the chemotherapeutic agent can be selected to maximize the devascularization of the tissue surrounding the tumor. Depending on various factors including the specific course of radiation and the specific tissue area or organ, this period of time can be, for example, at least a month. The isolated area can be, for example, an artery that is in proximity to the tumor. In some embodiments, a catheter device can be used to isolate the area. The catheter device can be used to increase the intraluminal pressure in the isolated artery. The isolated area can be, for example, the area of tissue involving the tumor. Examples of suitable chemotherapeutic agents include doxorubicin, erlotinib hydrochloride, everolimus, 5-FU, flurouracil, folfirinox, gemcitabine hydrochloride, gemcitabine-cisplatin, gemcitabine-oxaliplatin, irinotecan hydrochloride liposome, leucovorin, mitomycin C, mitozytrex, mutamycin, oxaliplatin, paclitaxel, paclitaxel albumin-stabilized nanoparticle formulation, or sunitinab malate or a combination of these drugs.

In some embodiments, a method of treating a cancerous tumor can involve: administering a course of radiation therapy to tissue including a solid tumor; isolating the proximal and the distal part of the vasculature closest to the tumor to produce an isolated arterial segment; decreasing the intraluminal pressure of the isolated arterial segment to the level of the interstitium; and administering a therapeutically effective dose of a chemotherapeutic drug. The course of the radiation therapy can decrease tissue efflux of the chemotherapeutic drug. In some embodiments, the vasculature can be isolated using a double balloon catheter positioned to exclude both the side and terminal branches of the artery. The chemotherapeutic drug can pass across the artery wall and into the surrounding tissue via a pressure gradient generated by the increase in the intraluminal pressure above the interstitial pressure. In some embodiments, the method can additionally include waiting a period of time following the step of administering the course of radiation therapy. The period of time between administration of the radiation therapy and administration of the chemotherapeutic agent can be selected to maximize the devascularization of the tissue surrounding the tumor. For example, depending on various factors including the specific course of administering the radiation therapy and the specific tissue region, this period of time can be at least two weeks. The targeted solid tumor can be, for example, a pancreatic tumor, a lung tumor, a brain tumor, a liver tumor, a uterine tumor, or a colon tumor. The chemotherapeutic drug can be, for example, a single chemotherapeutic or a combination of chemotherapeutic drugs.

Figure 5:
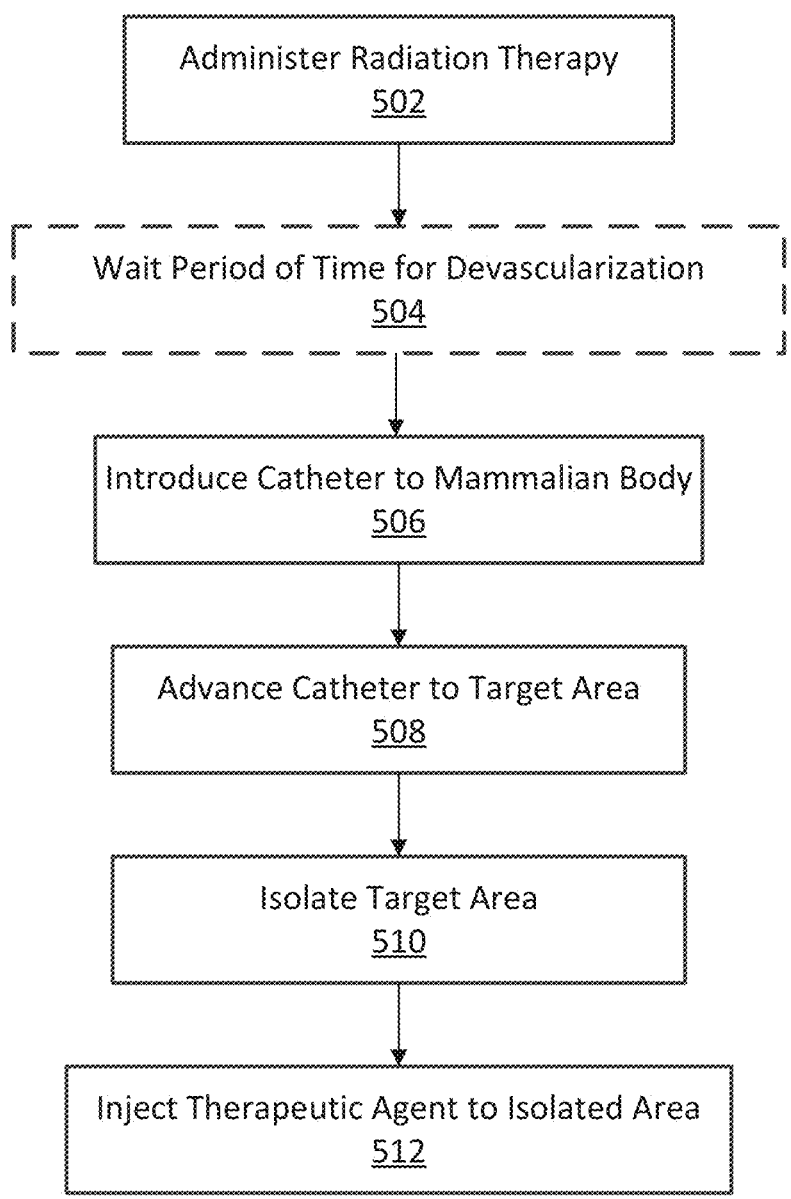
FIG. 5 is a flowchart illustrating a method for treating a cancerous tumor, according to embodiments described herein.

FIG. 5 is a flowchart illustrating a method 500 of treating a tumor involving the use of radiation. In particular, the method involves administering a course of radiation therapy to a target area, at 502. For example, an amount of radiation (e.g., 20-50 Gy) can be administered to a patient in multiple sessions (e.g. 1-25 sessions) over a period of time (e.g., a few days to six months). The target area can be a tissue area including a tumor. The method then optionally includes waiting a period of time for the radiation therapy to devascularize the tissue in the target area, at 504.

The method 500 further includes introducing a catheter (e.g., the catheter device 100) into a mammalian body into a bodily lumen (e.g., artery), at 506. The catheter can be advanced to a target area, at 508, and used to isolate the target area, at 510. In some embodiments, the catheter can include two occlusion members (e.g., occlusion elements 102, 104) that can be deployed (e.g., inflated) to isolate a segment of the bodily lumen to exclude the segment from its side and terminal branches. After the occlusion elements are deployed, an agent can be injected through an injection port of the catheter device to the isolated segment disposed between the two occlusion members, at 512. In some embodiments, a contrast dye can be can be injected into the isolated segment and the surrounding area can be visualized to determine whether the segment has been correctly isolated. For example, the injection of contrast through the infusion port can ensure that no extra vessels or bodily lumens are included in the isolated area. If desired, the catheter can be moved and the procedure repeated until the clinician can confirm that the catheter is correctly positioned. After the positioning of the catheter is confirmed, a therapeutic cell/biologic/agent can be introduced to the isolated segment through the infusion port.

In some embodiments, the step of administering the radiation therapy (502) can occur during and/or after the steps of introducing the catheter into the mammalian body (506), advancing the catheter to the target area (508), isolating the target area (510), and/or injecting a therapeutic agent into the target area (512). In some embodiments, one or more steps of the method 500 can be repeated before, during, and/or after other steps of the method 500.

Figure 6A:
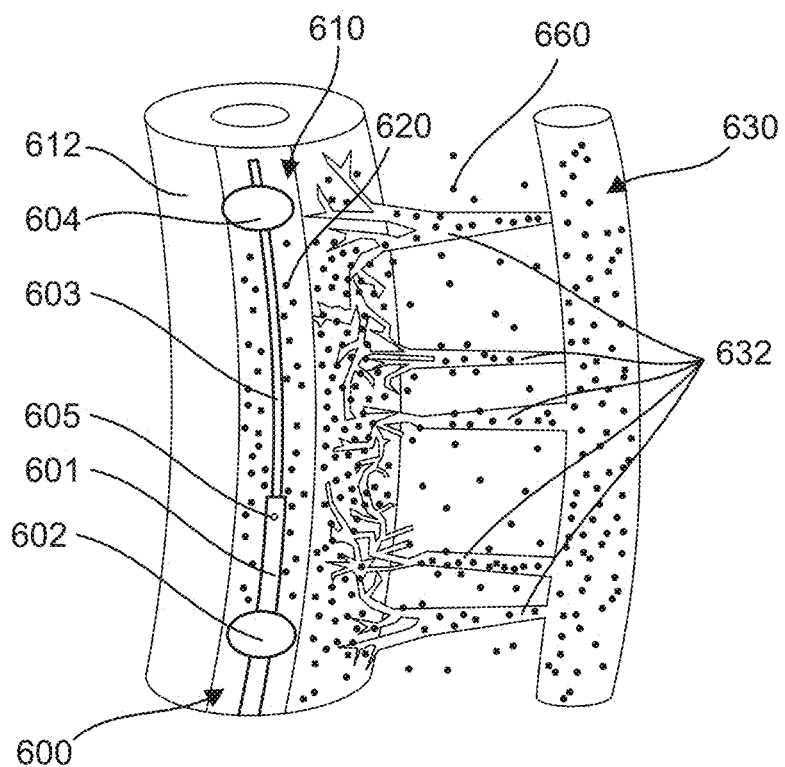
FIG. 6A is an illustration of dispersal of an infused agent into tissue surrounding a vessel without application of radiation therapy.
Figure 6B:
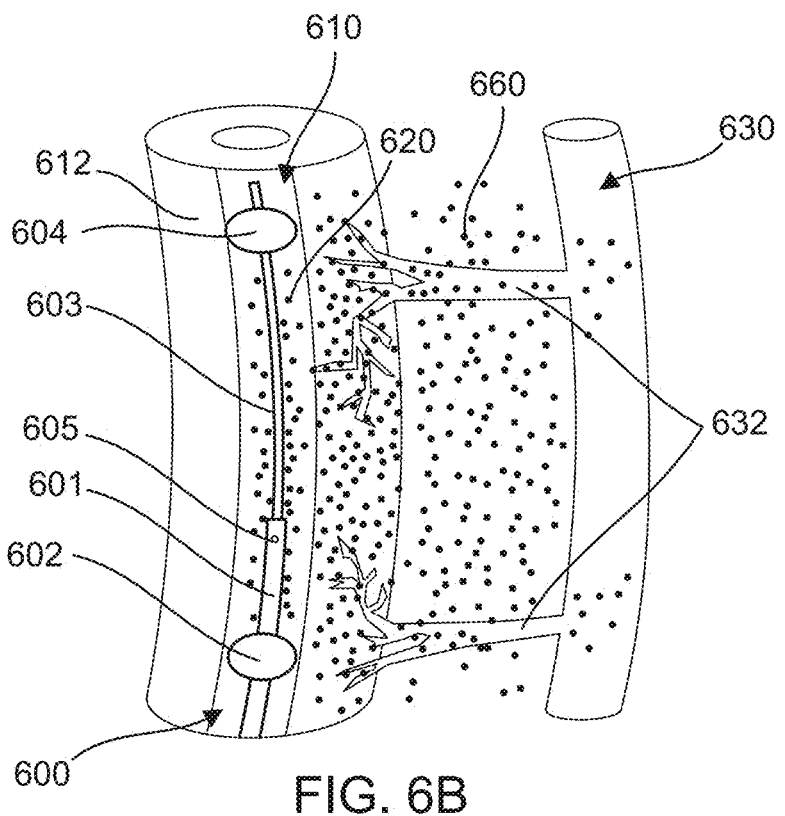
FIG. 6B is an illustration of dispersal of an infused agent into tissue surrounding a vessel with application of radiation therapy, according to embodiments described herein.

FIGS. 6A and 6B schematically illustrate the effects of radiation on the vasa vasorum microvasculature in tissue surrounding an isolated segment 620 of a bodily lumen 610. By reducing the microvasculature, the radiation therapy reduces drug washout and increases drug tissue concentration when a drug is delivered to the area using methods described herein, such as, for example, TAMP. FIG. 6A depicts an area of tissue surrounding an isolated segment 620 of a bodily lumen 610 prior to radiation therapy. FIG. 6B depicts the area of tissue after radiation therapy. After the radiation, the number of microvasculature connections 632 (e.g., micro-vessels extending from the isolated section 620 to the venous system 630) is reduced, thereby allowing a greater concentration of an infused drug 660 to remain in the tissue area.

As depicted in FIGS. 6A and 6B, a catheter device 600 can be used to deliver the infused drug 660 to the target area. The catheter device 600 can be similar to other catheter devices described herein (e.g., catheter device 100 and catheter device 300). For example, the catheter device 600 has a first occlusion element 602 and a second occlusion element 604, which are coupled to distal end portions of a first catheter 601 and a second catheter 603, respectively. The catheter device 600 also includes a port 605 for delivering the infused drug 660 to the isolated segment 620 between the first occlusion element 602 and the second occlusion element 604. Once the infused drug 660 is delivered to the isolated segment 620, it can pass through a wall 612 of the bodily lumen 610 into surrounding tissue.

Radiation Therapy

In methods described herein, radiation therapy can include, for example, external-beam radiation therapy delivered by X-rays, gamma rays, proton beams, or other appropriate sources. Radiation therapy damages cells by destroying the genetic material that controls how cells grow and divide. While both healthy and cancerous cells are damaged by radiation therapy, the goal of radiation therapy is to destroy as few normal, healthy cells as possible. The radiation therapy described herein can be targeted as narrowly as possible to the solid tumor(s) being treated or the tissue closely surrounding the solid tumor(s).

Typically, a radiation treatment plan is individualized for a patient, based upon detailed imaging scans showing the location of a patient's tumor(s) and the normal areas around it. The amount of radiation that normal tissue in different parts of the body can safely receive is known to one skilled in the art. Computed tomography (CT) scans are most frequently employed, but magnetic resonance imaging (MRI), positron emission tomography (PET), and ultrasound scans may also be used. A radiation oncologist determines the exact area that will be treated, the total radiation dose that will be delivered to the tumor, how much dose will be allowed for the normal tissues around the tumor, and the safest angles (paths) for radiation delivery. Radiation doses for cancer treatment are measured in Gy, which is a measure of the amount of radiation energy absorbed by one kilogram of human tissue. Different doses of radiation are needed to kill different types of cancer cells. Patients can receive external-beam radiation therapy in daily treatment sessions over the course of several weeks. The number of treatment sessions depends on many factors, including the total radiation dose that will be given. For example, one dose, which constitutes a fraction of the total planned dose of radiation, can be given each day. In a different instance, two treatments a day can be given.

As will be appreciated by one skilled in the art, the course of radiation therapy appropriate for use in the method of the present invention will depend on the specific cancerous tumor being treated. The specific dose of radiation, the duration of the radiation, and the number of treatments for any particular individual will depend upon a variety of factors including the type of cancer, the size of the tumor(s), and the patient's age and medical history including, for example, the amount of radiation previously received. Concurrent chemotherapy may also impact the dose of radiation given.

When treating a pancreatic cancer, for example, the course of radiation therapy can be approximately 20 to 50 Gy of radiation delivered in approximately one to 25 treatments over approximately one to five weeks. Alternatively, two to five sessions of radiation can be given over a period of approximately a week. For certain types of cancer, the amount of radiation therapy delivered may be as low as one Gy. In preferred embodiments, the course of radiation therapy can be approximately 40 to 50 Gy of radiation delivered in approximately 22 to 25 treatments over approximately four to five weeks. As may be appreciated by one skilled in the art, the amount of radiation therapy useful in methods described herein is that necessary to devascularize the solid tumor of interest thus allowing the TAMP technique to be used advantageously.

In methods described herein, after administering the radiation therapy, a physician may wait for a period of time before administering chemotherapy such that the tumorous tissue can die (e.g., necrosis) or become devascularized. In some embodiments, this period of time can be selected to maximize devascularization of the solid tumor and/or tissue containing the solid tumor. In some embodiments, this period of time can be selected to maximize the effect of the chemotherapy based on a sufficient amount of devascularization. In certain instances, the time period that elapses before administering chemotherapy can be at least a month. In other instances, the period of time is approximately two weeks to six months.

Chemotherapeutics

Specific chemotherapeutics can be selected based on the particular solid cancerous tumor that is to be treated. For example, the following chemotherapeutic agents and others may be used in the treatment of pancreatic cancer: doxorubicin, erlotinib hydrochloride, everolimus, 5-FU, flurouracil, folfirinox, gemcitabine hydrochloride, gemcitabine-cisplatin, gemcitabine-oxaliplatin, irinotecan hydrochloride liposome, leucovorin, mitomycin C, mitozytrex, mutamycin, oxaliplatin, paclitaxel, paclitaxel albumin-stabilized nanoparticle formulation, or sunitinab malate. In some embodiments, a combination of agents may be employed. For example, when treating pancreatic cancer, a combination of gemcitabine hydrochloride (Gemzar®) and paclitaxel albumin-stabilized nanoparticle formulation (Abraxane®) may be used.

The above-described chemotherapeutic agents are available from a variety of corporate sources licensed to provide such agents for human use. Generic formulations of non-proprietary chemotherapeutics are typically available from a variety of manufacturers. A list of these licensed suppliers is available from the U.S. Food and Drug Administration's "Approved Drug Products with Therapeutic Evaluations," commonly known as the "Orange Book" (http://www.accessdata.fda.gov/scripts/cder/ob/). Proprietary chemotherapeutics are typically available from one manufacturer, also identifiable in the Orange Book. For example, the corporate source for Gemzar® is Eli Lilly and Company (Indianapolis, Ind.) and Celgene Corporation (Summit, N.J.) supplies Abraxane®.

Methods described herein can use an amount of chemotherapeutic agent that is known to be therapeutically effective at treating a tumor. For example, the amount of chemotherapeutic agent that is used can be based on the Prescribing Information for a particular chemotherapeutic drug. A physician can adjust the amount of the chemotherapeutic agent to an amount that is appropriate for use with the TAMP techniques described herein.

In methods described herein, a therapeutic agent (e.g., chemotherapy drug) can be delivered via rapid infusion (e.g., injected directly into an artery over a period of minutes, intravenous infusion (e.g., through a drip or pump over a period of approximately 20 minutes to a few hours), or continuous infusion (e.g., through a continuation infusion pump over a period of weeks to months). The infusion of the drug into an isolated space increases the intraluminal or interior pressure of the vessel to above the interstitial pressure of the surrounding tissue and the pressure gradient forces the drug across a vessel wall and into the surrounding tissue.

Catheter Device

In some embodiments, methods described herein can use a catheter device such as, for example, a double occlusion balloon to isolate a segment of a bodily lumen (e.g., artery) and allow infusion of a therapeutic agent (e.g., chemotherapy drug) into the isolated segment between the balloon after they are inflated. For example, methods disclosed herein may use catheter devices such as those described in U.S. patent application Ser. No. 14/293,603, filed Jun. 2, 2014, titled "Devices, methods and kits for delivery of therapeutic materials to a target artery," now issued as U.S. Pat. No. 9,457,171, and U.S. patent application Ser. No. 14/958,428, filed Dec. 3, 2015, titled "Occlusion catheter system and methods of use," which are incorporated herein by reference. Briefly, a catheter device suitable for isolating a section of a bodily lumen near a solid tumor includes, but is not limited to, features and functions such as, for example: (1) selective isolation of the targeted portion of the portion of the artery for targeted delivery of the therapeutic agent to the solid tumor; (2) an infusion port allowing first, injection of contrast into the isolated segment to allow direct visualization of the origin of the branches of the artery supplying the cancerous tissue, and second, introduction of chemotherapeutic drugs; and (3) a self-contained assembly unit with easy retrieval after completion of the procedure. In one embodiment, the catheter device includes expandable occlusion elements in the form of inflatable balloons that can be used to isolate a proximal and distal end of a bodily lumen of interest.

Methods described herein can include, for example, introducing a catheter device into a splenic artery of the pancreas. The catheter device can have, for example, two lumens—one for inflation/deployment of the balloons/occluding elements and a second for introduction of the infusate (e.g., therapeutic agent) to the space between the two balloons. The catheter can be advanced to a target portion of the splenic artery. A region of the target portion of the splenic artery is selectively isolated and the infusate is injected into the isolated region. In some embodiments, the method can include advancing at least a portion of the catheter device to an ostium of a celiac artery, its hepatic branch (and its branches), or if necessary, the superior mesenteric artery, depending on a patient's anatomy. In some embodiments, a contrast dye is injected into the isolated region to confirm exclusion of side branches before injecting the infusate.

In some embodiments, the catheter device can have one or more features to achieve a desired effect on a specific anatomy of tumors. For example, there may be: (1) a separate inflation lumen for the proximal and the distal occluders/balloons to allow different size occluders/balloons proximally and distally; (2) slidable catheters to allow the distance between the occluders/balloons to be adjusted; and (3) a sensor at the tip to monitor pressure in the isolated segment of the bodily lumen.

FIGS. 4A and 4B schematically depict an example of a catheter device 300 disposed within a bodily lumen 310 (e.g., artery) and the dispersal of an infused substance 360 through the bodily lumen 310 into surrounding tissue. The catheter device 300 can be similar to other catheter devices (e.g., catheter device 100) described herein. For example, catheter device 300 includes a first occlusion element 302 and a second occlusion element 304 for occluding a portion 320 of bodily lumen 310. The first occlusion element 302 is coupled to a distal end portion of a first catheter 301, and the second occlusion element 304 is coupled to a distal end portion of a second catheter 303. The occlusion elements 302, 304 are filter elements that can be moved between a collapsed configuration for insertion of the catheter device 300 into a body of a patient (e.g., into an artery) and an expanded or dilated configuration, as shown in FIGS. 4A and 4B, for occluding a portion of a bodily lumen. The occlusion elements 302, 304 when in the collapsed configuration have a smaller outer perimeter (or diameter) than when in the expanded configuration.

As depicted in FIGS. 4A and 4B, the catheter device 300 can be used to isolate a segment 320 of a bodily lumen 310 within the space defined between the first occlusion element 302 and the second occlusion element 304. The catheter device 300 can include a lumen in fluid communication with port or opening 305 for delivering an agent 360 (e.g., a dye or a chemotherapy drug) to the space between the first occlusion element 302 and the second occlusion element 304. The first catheter 301 can define the lumen and the opening 305. The opening 305 can be disposed on the distal end portion of the first catheter 301 distal to the first occlusion element 302. The second catheter 303 can be movably disposed within a lumen defined by the first catheter 301 such that the second catheter 303 can be moved relative to the first catheter 301 to move the second occlusion element 304 relative to the first occlusion element 302. According to some embodiments of the disclosure, the second occlusion element 304 can be moved toward the first occlusion element 302 to increase pressure within the isolated segment 320. The increased pressure can be used, for example, to drive delivery of the agent 360 through the wall 312 of the bodily lumen 310 and into the surrounding tissue.

In some embodiments, the catheter device 310 can have a sensor such as a pressure transducer 306 that may assist with achieving an optimal pressure within an occluded arterial segment for optimizing trans-arterial diffusion of an infused substance during a method of cancer treatment (e.g., a TAMP procedure). The pressure transducer 306 may be disposed along the catheter device 300 in the isolated arterial segment 320 (e.g., disposed between the first occlusion element 302 and the second occlusion element 304 (as depicted in FIGS. 4A and 4B)). The pressure transducer 306 can be disposed on one of the catheters 301, 303, or disposed on one of the occlusion elements 302, 304. The pressure transducer 306 can be designed to measure an intraluminal pressure of the isolated segment 320. The pressure measurements may be used to adjust the intraluminal pressure of the isolated segment 320 to a predetermined or optimal pressure level. A physician may use the pressure measurements to determine a rate of infusing a drug or other therapeutic material into the isolated segment 320 in order to decrease or increase the intraluminal pressure of the isolated segment

320. For example, a physician can increase the rate of infusion of a drug to increase the intraluminal pressure of the isolated segment 320 above the pressure of tissue surrounding the isolated segment 320 (e.g., above the pressure of the interstitium) to create a pressure gradient between the intraluminal space and the surrounding tissue to increase permeation of the infused drug through the arterial wall and into the tissue. Additionally or alternatively, a physician can increase or decrease the intraluminal pressure of the isolated segment 320 by adjusting the position of the two occlusion elements 302, 304 relative to one another (e.g., moving the two occlusion elements 302, 304 closer or further apart from one another).

Determination of Therapeutic Effectiveness

The efficacy of the methods of the present invention in the treatment of solid cancerous tumors can be evaluated in human clinical trials conducted under appropriate standards and ethical guidelines as set forth by the U.S. Food and Drug Administration (FDA). Such studies are conducted according to U.S. and International Standards of Good Clinical Practice. Typically, such trials are comparison trials, in that the method of the present invention is utilized in one cohort of patients, while one or more other cohorts receive alternative methods of treating the tumors. The alternative methods can include, for example, treatment with systemic chemotherapy alone.

A clinical trial for the treatment of cancerous tumors may have a primary objective of evaluating survival in patients who undergo radiation therapy followed by intra-arterial delivery of a chemotherapeutic agent to an isolated arterial section near the solid tumor after a suitable interval of time elapses. The second objective of such a trial is to assess tumor response by known imaging techniques at the primary site of application of the chemotherapeutic agent. In particular, the size of the tumor before and after treatment can be determined and evaluated across different treatment methods. In addition, the conversion rate from unresectable or borderline resectable to potentially resectable or resectable tumors can be determined. The results may be analyzed using standard statistical techniques known to those skilled in the art.

The following examples, including clinical studies, are offered by way of illustration and not by way of limitation.

Examples: Experiments with Pig Tissue

Figure 7:
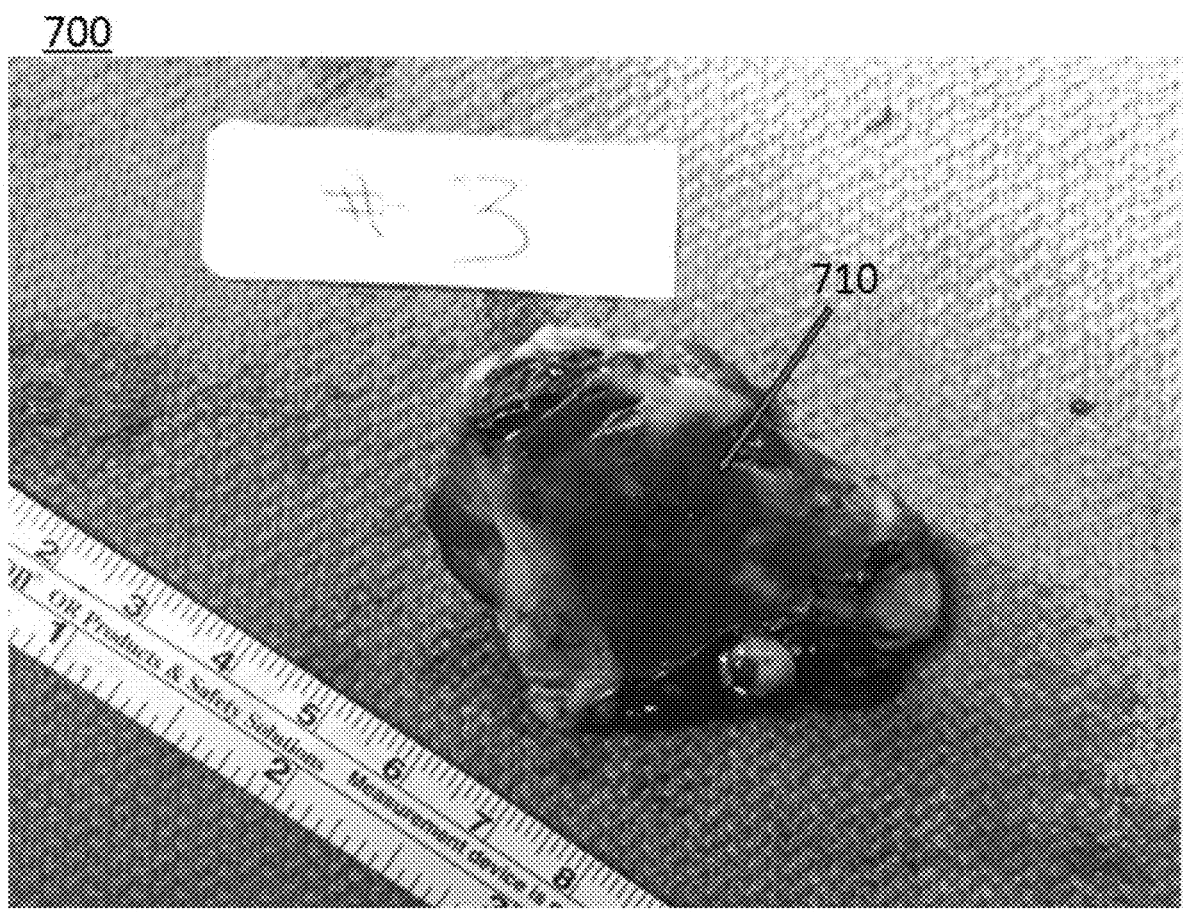
FIG. 7 is an image of a pancreatic tumor after undergoing treatment according to methods described herein.

FIG. 7 is an image 700 of a pancreatic tumor 710 of a pig after treatment with the TAMP method. The method involved occluding the celiac artery of the pig with a double balloon catheter, rapidly infusing dye at six milliliters per minute for ten minutes into the isolated segment of the celiac artery, and harvesting the tissue next to the celiac artery. As depicted, the infused dye has permeated into the harvested tissue.

Figure 8:
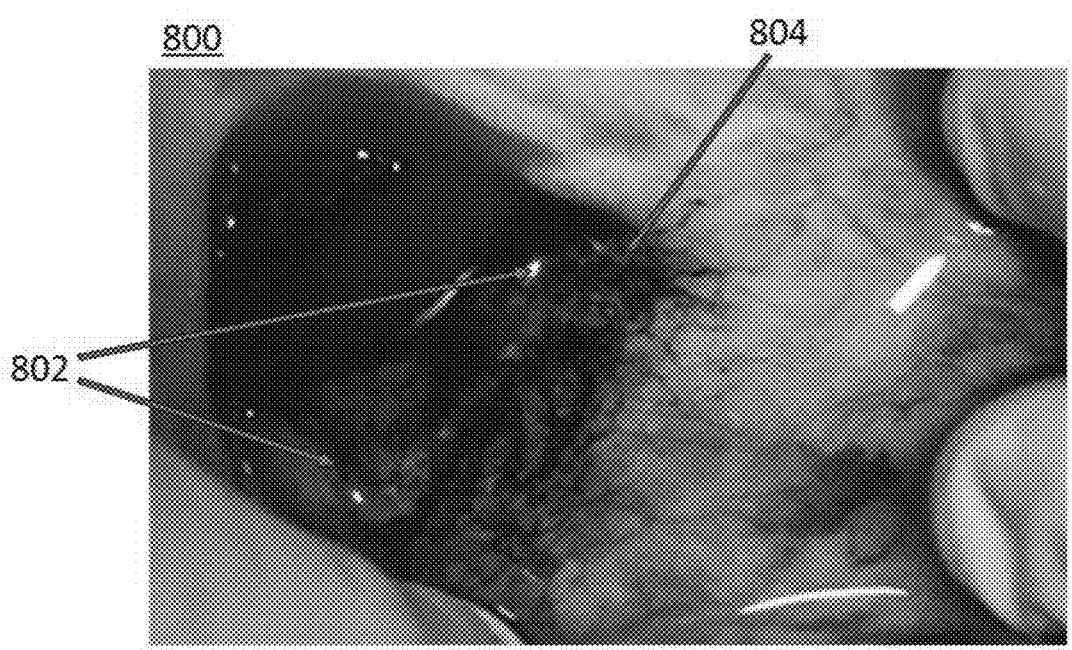
FIG. 8 is an image showing penetration of infused agents into tissue surrounding a vessel via the microvasculature, according to an embodiment.

FIG. 8 is an image 800 of tissue surrounding the celiac artery of a pig after treatment with the TAMP method. The method involved occluding the celiac artery of the pig with a double balloon catheter (i.e., a balloon catheter with occlusion elements or balloons 802) and rapidly infusing dye at six milliliters per minute for ten minutes into the isolated segment of the celiac artery. The image shows the tissue surrounding the celiac artery in situ within ten sections after initiating the rapid infusion of the dye. As depicted in FIG. 8, the dye 804 has penetrated into the surrounding tissue via the vasa vasorum microvasculature.

Figure 11:
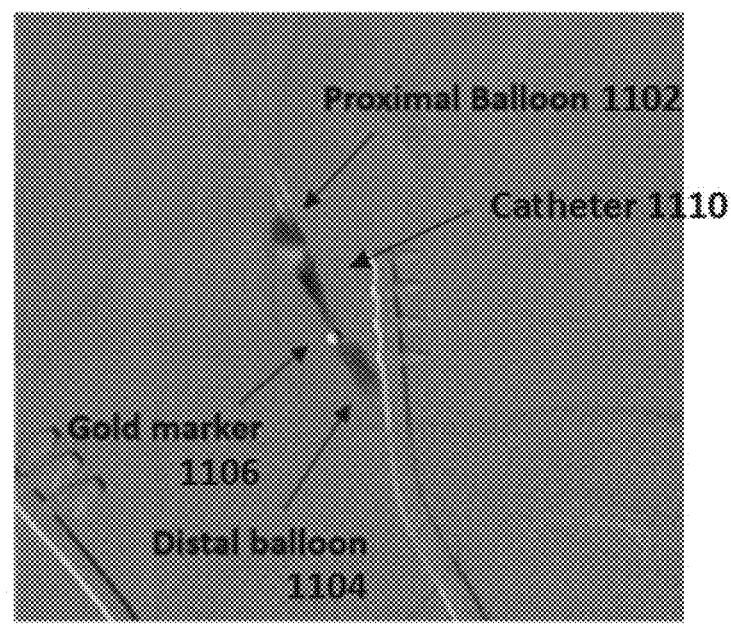
FIG. 11 is an image of a catheter device disposed in a vessel in a patient's groin area, according to an embodiment.
Figure 12:
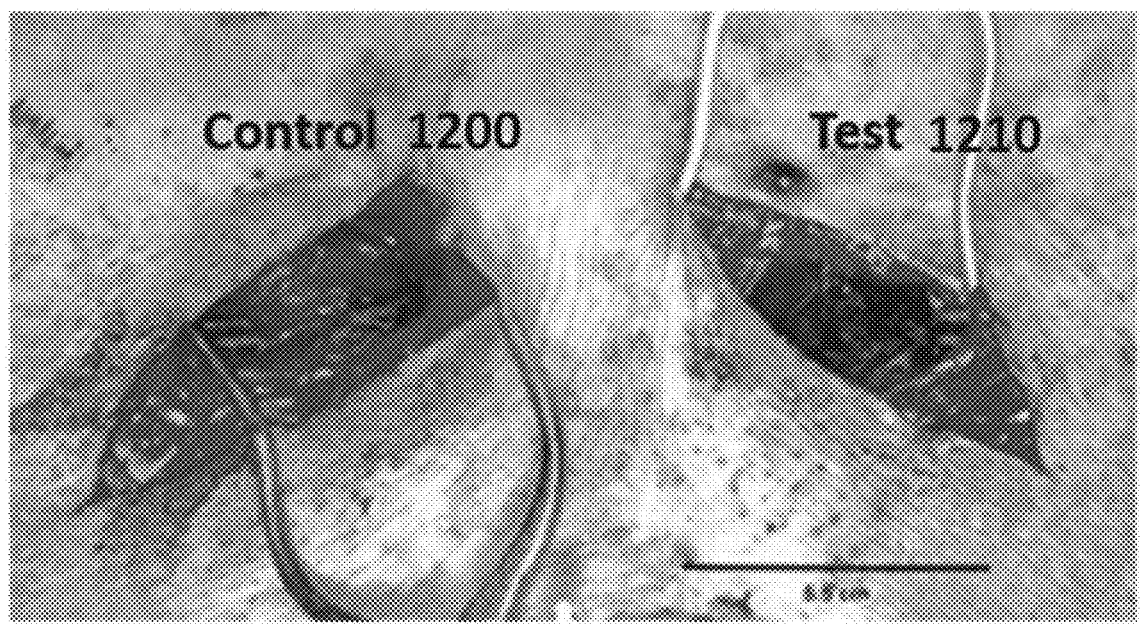
FIG. 12 is an image showing penetration of an infused agent into tissue surrounding a vessel after undergoing treatment, according to an embodiment.

FIGS. 11 and 12 relate to an experiment conducted on a pig to evaluate the effect of radiation on tissue penetration of drugs/molecules using the TAMP technique. The experiment involved administering radiation treatment to a left groin area in a pig and comparing the penetration of a dye introduced using the TAMP technique in the left groin area (referred to herein as the test 1200) versus the penetration of the dye in the right groin area (referred to herein as the control 1210). A Yucatan pig was anesthetized for a CT scan of the femoral artery to plan the radiation treatment. Both femoral arteries were accessed for the placement of sterile gold fiducial markers to mark the areas of interest for comparison following the radiation treatment and infusion of dye. The left groin area was treated with a single radiation session using the CyberKnife® system at 15 Gy outside the artery adjacent to the gold marker. FIG. 11 depicts an image 1100 of the left groin area with the gold marker 1106. One month following radiation treatment, with the animal under general anesthesia, a percutaneous exposure of the left and right femoral artery was completed. From the left carotid artery, a double balloon catheter 1110 was advanced to the area of the left femoral artery and a proximal balloon 1102 and a distal balloon 1104 of the catheter 1110 were positioned and inflated adjacent to the gold fiducial marker 1106, as shown in FIG. 11. The catheter 1110 isolated the relevant segment of the left femoral artery adjacent to the gold fiducial marker 1106 to ensure exclusion of any large side branches and to achieve optimal intravascular pressure in the isolated segment. A syringe pump was then used to inject a dye at six milliliters per minute for approximately 30 seconds through an infusion port between the two balloon catheters. The same procedure was repeated for the right femoral artery. At the conclusion of the procedures in the left and right femoral arteries, the area of dye penetration around the blood vessels were measured. As shown in FIG. 12, there was approximately a three-fold increase in penetration on the irradiated left side (i.e., test 1200) as compared to the control right side (i.e., control 1210).

Examples: Clinical Studies of Treating Pancreatic Cancer

A post-market registry study was conducted to assess patient survival and clinical outcomes using the RenovoCath™ RC120 catheter (RenovoRx, Los Altos, Calif.) in a clinical, prospective observational setting when used to deliver a chemotherapeutic to the pancreas as described in Table 1.

TABLE 1

| | |
|---|---|
| Study Title: | Inter-Arterial Treatment of Pancreatic Cancer Using the RenovoCath ™ RC120 Catheter |
| Development Phase: | Post market |
| Study Type: | Global Multicenter, Prospective, Observational Registry |
| Product Description: | The RenovoCath ™ RC120 Catheter is an endovascular multi-lumen, two handled catheter designed to isolate variable segments of arteries supplying the target organ using two slideable, compliant balloons. |
| Study Population: | Patients with pancreatic cancer, with and without prior radiation therapy |
| Chemotherapeutic agent: | Gemcitabine injection (Gemzar ®) |
| Primary Objectives | 1. Evaluate survival in patients diagnosed with pancreatic cancer who undergo intra-arterial delivery of chemotherapeutic agents to the pancreas<br>2. Assess tumor response in the primary site of application as assessed by imaging |

TABLE 1-continued

| | |
|---|---|
| Primary Endpoints | 1. Survival<br>2. Tumor response<br>3. Performance of RenovoCath in defined population (pancreatic cancer) in a clinical setting |
| Secondary Objective/ Endpoints | 1. Assess conversion rate from unresectable or borderline resectable to potentially resectable or resectable pancreatic cancer<br>2. Further define and analyze potential selection criteria for patients who present with locally advanced pancreatic cancer that may benefit from the intra-arterial procedure |
| Study Sites: | Multicenter |

After patient screening and enrollment, eligible patients underwent selective catheterization introduced via the femoral artery into the celiac axis into the splenic, hepatic and/or superior mesenteric artery(ies) using the TAMP technique as described above for the localized delivery of gemcitabine followed by embolization agent lipiodol. An interventional radiologist used the RenovoCath™ RC 120 catheter to optimize drug delivery to the tumor(s). At the conclusion of the case, the femoral artery arteriotomy was sealed and patient monitored as per standard institutional protocol.

All patients enrolled during the two-year registry enrollment period were followed periodically for survival outcome. Patients were contacted by telephone at the following intervals after the final intra-arterial treatment: 6 months±30 days, 1 year±30 days and 2 years±30 days. Patients were assessed for serious adverse events with specific attention to events related to local delivery of chemotherapeutic agents to the pancreas and device performance.

Figure 9:
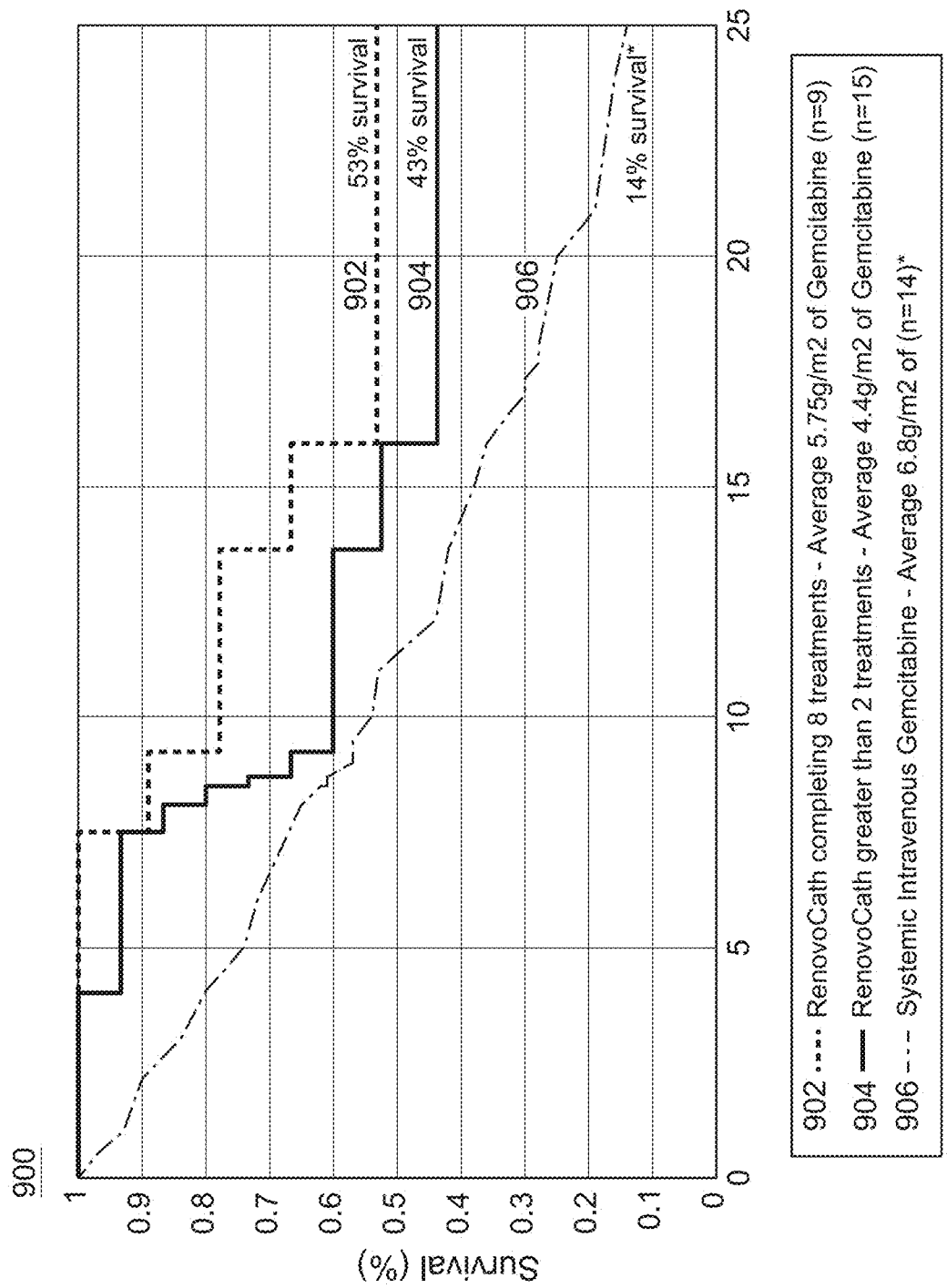
FIG. 9 is a graph comparing survival rates of patients treated according to different methods described herein.

FIG. 9 shows the superiority of the TAMP technique as compared to standard systemic chemotherapy. Graph 900 shows the increase in survival benefits in patients treated with TAMP compared to those treated with a systemic intravenous infusion of the same drug (i.e., gemcitabine). Line 902 represents the survival percentage of patients completing eight treatments of gemcitabine using the TAMP technique. Line 904 represents the survival percentage of patients completing more than two treatments of gemcitabine using the TAMP technique. And line 906 represents the survival percentage of patients given systemic infusion of gemcitabine, the results of which are taken from Chauffert et al., *Ann. Oncol.*, 2008, 19:1592-9. As depicted in FIG. 9, the survival rates of the patients treated with the TAMP technique (i.e., lines 902, 904) were greater than the survival rates of the patients given systemic infusion of the same drug (i.e., line 906).

Figure 10:
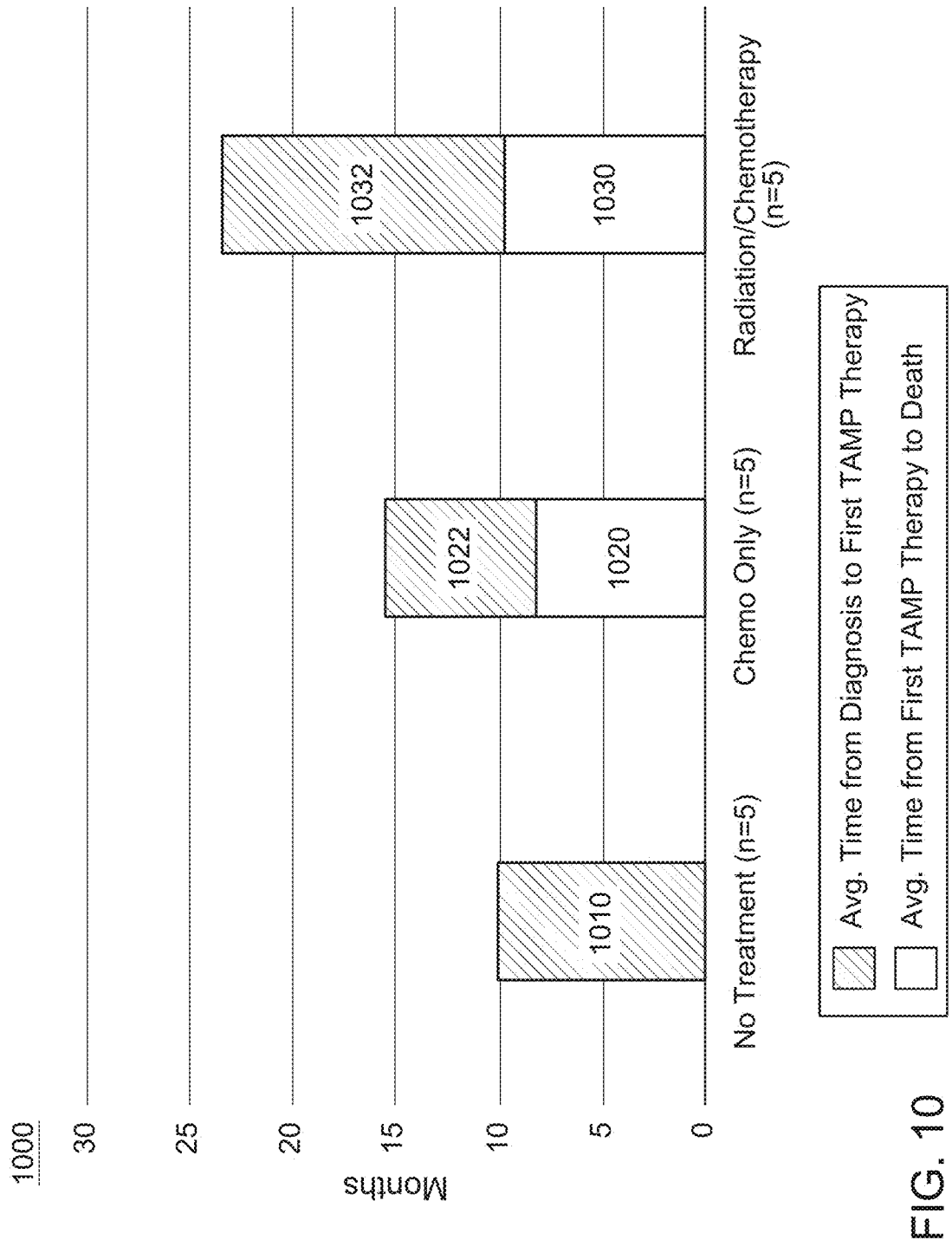
FIG. 10 is a bar chart comparing survival rates of patients treated according to different methods described herein.

FIG. 10 is a graph 1000 illustrating the effect of the TAMP technique on patient survival after radiation therapy compared with the effect of the TAMP technique with no radiation therapy. Fifteen patients with locally advanced pancreatic cancer were treated with gemcitabine in a dose-escalated protocol administered in four cycles using the TAMP technique. Each cycle consisted of two treatments two weeks apart. The efficacy data for the fifteen patients who received more than one cycle of TAMP treatment are shown in FIG. 6. Of these fifteen patients, five had no prior treatment of any kind, five had prior systemic chemotherapy, and five received radiation in additional to systemic chemotherapy prior to entering the study. On average, patients received radiation one to six months prior to enrolling in the study and receiving TAMP therapy. For the three groups of patients, the most pronounced survival benefit was seen in patients who had received radiation prior to the initiation of TAMP therapy. Specifically, patients with prior radiation had a significant improvement in survival compared to the ones that had either no prior treatment or only prior systemic chemotherapy with no radiation therapy. Patients were treated with TAMP therapy, regardless of their prior history. The dotted portion of the bars (1020, 1030) indicates the average time from diagnosis to the first TAMP therapy, while the clear portion of the bars (1010, 1022, 1032) indicates the average time from the first TAMP therapy to death.

This study demonstrated that a course of radiation prior to chemotherapy treatment administered via the TAMP technique has significant clinical benefit in patients with locally advanced pancreatic cancer. Combining these two modalities led to significant increase in median survival, reduction of tumor markers, and downsizing of the tumor. It is expected that a similar combination therapy would have clinical benefit in any solid tumors where diffusion-dependent infusion of a chemotherapeutic may be considered as a treatment option.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above. For example, the size and specific shape of the various components can be different from the embodiments shown, while still providing the functions as described herein. Furthermore, each feature disclosed herein may be replaced by alternative features serving the same, equivalent or similar purpose, unless expressly stated otherwise. Thus, unless expressly stated otherwise, each feature disclosed is one example only of a generic series of equivalent or similar features.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed is:

1. A method, comprising:
   devascularizing a target area including a tumor to reduce the microvasculature in the target area by administering a dose of radiation to the target area;
   inserting a catheter device into a vessel, the catheter device including a first occluder and a second occluder;
   isolating a segment of the vessel proximate to the target area using the first occluder and the second occluder;
   delivering a dose of an agent to the devascularized target area from the isolated segment via the catheter device.

2. The method of claim 1, wherein the agent is a chemotherapeutic agent.

3. The method of claim 2, wherein the chemotherapeutic agent includes one or more compounds selected from a group consisting of: doxorubicin, erlotinib hydrochloride, everolimus, 5-FU, flurouracil, folfirinox, gemcitabine hydrochloride, gemcitabine-cisplatin, gemcitabine-oxaliplatin, irinotecan hydrochloride liposome, leucovorin, mitomycin C, mitozytrex, mutamycin, oxaliplatin, paclitaxel, paclitaxel albumin-stabilized nanoparticle formulation, and sunitinab malate.

4. The method of claim 2, wherein the chemotherapeutic agent includes at least two compounds selected from a group consisting of: doxorubicin, erlotinib hydrochloride, everolimus, 5-FU, flurouracil, folfirinox, gemcitabine hydrochloride, gemcitabine-cisplatin, gemcitabine-oxaliplatin, irinotecan hydrochloride liposome, leucovorin, mitomycin C, mitozytrex, mutamycin, oxaliplatin, paclitaxel, paclitaxel albumin-stabilized nanoparticle formulation, and sunitinab malate.

5. The method of claim 1, wherein the catheter device defines a lumen and an infusion port, the lumen in communication with the infusion port and configured to deliver the dose of the agent to the segment.

6. The method of claim 5, wherein the infusion port is disposed on the catheter device between the first occluder and the second occluder such that the infusion port can deliver the dose of the agent to the segment isolated between the first occluder and the second occluder.

7. The method of claim 1, wherein the tumor is a pancreatic tumor.

8. The method of claim 1, wherein the insertion of the catheter device into the vessel occurs after the administering of the dose of radiation.

9. The method of claim 1, wherein the delivery of the dose of the agent occurs after a predefined period of time following the administering of the dose of radiation.

10. The method of claim 9, wherein the predefined period of time is between two weeks and six months.

11. The method of claim 1, further comprising administering one or more additional doses of radiation to the target area,
wherein the dose of radiation and the additional doses of radiation are administered during a period of one to five weeks, and
wherein the dose of radiation and the additional doses of radiation include an amount of radiation totaling between 20 and 50 gray (Gy).

12. The method of claim 11, wherein the amount of radiation is selected based on one or more characteristics of the tumor, the one or more characteristics including at least one of: a location of the tumor, and a size of the tumor.

13. The method of claim 1, wherein the dose of the agent is a first dose of a first agent, and further comprising delivering a second dose of a second agent to the isolated area of the artery.

14. The method of claim 13, wherein the first agent is a dye and the second agent is a chemotherapeutic agent.

15. The method of claim 13, wherein the first agent is a first chemotherapeutic agent and the second agent is a second chemotherapeutic agent different from the first chemotherapeutic agent.

16. A method, comprising:
devascularizing a target area including a tumor to reduce the microvasculature in the target area by administering a dose of radiation to the target area;
isolating a segment of a vessel proximate to the target area;
decreasing an intraluminal pressure of the segment to a level of pressure of an interstitial space between the vessel and the target area; and
delivering a dose of an agent to the devascularized target area from the isolated segment via a catheter device while increasing the intraluminal pressure to greater than the pressure of the interstitial space between the vessel and the target area.

17. The method of claim 16, wherein the segment of the vessel is isolated using a catheter device including a first occluder and a second occluder.

18. The method of claim 17, wherein the catheter device further includes a pressure sensor configured to measure the intraluminal pressure of the segment.

19. A method, comprising:
devascularizing a target area to reduce the microvasculature in the target area, the target area including a tumor;
inserting a catheter device into a vessel, the catheter device including a first occluder and a second occluder;
isolating a segment of the vessel proximate to the target area using the first occluder and the second occluder;
delivering a dose of an agent to the devascularized target area from the isolated segment via the catheter device.

* * * * *